United States Patent [19]
Shturman et al.

[11] Patent Number: 6,039,747
[45] Date of Patent: Mar. 21, 2000

[54] ROTATIONAL ATHERECTOMY DEVICE WITH IMPROVED OPTICAL TACHOMETER

[75] Inventors: Leonid Shturman, Minneapolis, Minn.; Georgiy Morov; Vladimir Malgichev, both of Moscow, Russian Federation

[73] Assignee: Shturman Cardiology Systems, Inc., Minneapolis, Minn.

[21] Appl. No.: 09/057,364

[22] Filed: Apr. 8, 1998

[51] Int. Cl.$^7$ .................................................. A61B 17/22
[52] U.S. Cl. ................................................................ 606/159
[58] Field of Search ..................................... 606/159, 180, 606/80, 167, 170, 171; 604/22

[56] References Cited

U.S. PATENT DOCUMENTS

| | | | |
|---|---|---|---|
| 4,990,134 | 2/1991 | Auth | 606/159 |
| 5,059,901 | 10/1991 | Van Voorhis. | |
| 5,217,474 | 6/1993 | Zacca et al. | 606/159 |
| 5,314,407 | 5/1994 | Auth et al. | 606/159 |
| 5,779,722 | 7/1998 | Shturman et al. | 606/159 |

FOREIGN PATENT DOCUMENTS

| | | |
|---|---|---|
| 0112143 | 6/1984 | European Pat. Off. . |
| 0380810 | 8/1990 | European Pat. Off. . |

*Primary Examiner*—Michael Buiz
*Assistant Examiner*—(Jackie) Tan-Uyen T. Ho
*Attorney, Agent, or Firm*—Fredrikson & Byron, P.A.

[57] ABSTRACT

A rotational atherectomy device having an improved optical tachometer which uses a single, monofilament optical fiber to both transmit light from a light source to a light reflector and to return reflected light to a light detector. A fiber optic connector which can be used with such a rotational atherectomy device permits one to releasably optically couple a distal end of an optical fiber to both a light source and a light detector via a beam splitter and a flexible light guide. This fiber optic connector may include a pneumatic clamp which is connected to the same source of compressed gas which drives the prime mover of the rotational atherectomy device.

18 Claims, 23 Drawing Sheets

ROTATIONAL ATHERECTOMY DEVICE WITH IMPROVED OPTICAL TACHOMETER

FIELD OF THE INVENTION

The invention relates to devices and methods for removing tissue from body passageways, such as removal of atherosclerotic plaque from arteries, utilizing a rotational atherectomy device. In particular, the invention relates to improvements in a rotational atherectomy device having an optical tachometer. This invention also has additional uses unrelated to atherectomy devices.

BACKGROUND OF THE INVENTION

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (Auth), a rotating burr covered with an abrasive cutting material, such as diamond grit (diamond particles or dust), is carried at the distal end of a flexible, rotatable drive shaft.

U.S. Pat. No. 5,314,438 (Shturman, the teachings of which are incorporated herein by reference) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

U.S. Pat. No. 5,314,407 (Auth, the teachings of which are incorporated herein by reference) shows details of a type of handle which may be used in conjunction with rotational atherectomy devices of the type shown in the Auth '134 and Shturman '438 patents. A handle of the type shown in the Auth '407 patent has been commercialized by Heart Technology, Inc. (Redmond, Wash.), now owned by Boston Scientific Corporation (Natick, Mass.) in the rotational atherectomy device sold under the trademark Rotablator®.

FIG. 1 schematically illustrates a Rotablator® atherectomy device. This atherectomy device generally includes an elongate, generally tubular handle A which slidably carries a prime mover carriage B. A compressed gas driven turbine (not shown) is carried by the prime mover carriage B. The turbine is connected to a drive shaft C having an abrasive-coated burr D at its distal end. The drive shaft and the burr are rotated at high speeds, typically in the range of about 140,000 to about 180,000 rpm. The drive shaft C is designed to be advanced over and rotated around a guide wire E, which is typically held in place using a pneumatic guide wire clamp (not shown) in the proximal end portion of the handle A. Most of the length of the drive shaft is disposed inside a catheter F.

The rotational speed of the compressed gas turbine of the Rotablator® device is determined by a fiber optic tachometer. This tachometer includes a fiber optic cable assembly G which is attached to the prime mover carriage B via a rigid dual fiber optic connector H. The fiber optic cable assembly G comprises two separate fiber optic cables—a first fiber optic cable I which carries light from a light source into the prime mover carriage B, and a second fiber optic cable J which carries light from the prime mover carriage back to a light detector. A proximal end portion of each of these fiber optic cables I and J is rigidly mounted in the dual fiber optic connector H. A distal end portion of each of these fiber optic cables is provided with a standard Hewlett-Packard type click-fit plug K to permit the first fiber optic cable I to be snap-fit into a light emitting diode module and the second fiber optic cable J to be snap-fit into a photodetector module.

FIGS. 2 and 3 are schematic cross sectional views through the Rotablator® device taken along line 2—2 of FIG. 1. As shown in these drawings, the dual fiber optic connector H comprises a metal fitting L which fixes the relative positions of the proximal end portions of the fiber optic cables I and J. A portion of a plastic jacket M is retained within the distal portion of the metal fitting L. As best seen in FIG. 3A, an outer crimping ring Q is used to secure the proximal end portions of the fiber optic cables I and J within the metal fitting L. The plastic jacket M is common to both of the fiber optic cables I and J. The metal fitting is rigidly secured within the prime mover carriage B to hold the ends of the two fiber optic cables I and J at a precise location within the prime mover carriage B.

The fiber optic tachometer of the Rotablator® device also includes a tachometer rotor N mounted on a shaft P of the prime mover. The rotor N has an exterior surface which is substantially non-reflective. The rotor also includes two generally hemispherical reflective surfaces O located on diametrically opposite sides of the rotor. As the rotor N rotates together with the prime mover shaft P within the prime mover carriage B, the rotor will move from a position wherein one of the reflective surfaces O is positioned adjacent the proximal ends of the fiber optic cables I and J (FIG. 2) to a position wherein the non-reflective exterior surface of the rotor is positioned adjacent the proximal ends of the fiber optic cables I and J (FIG. 3).

SUMMARY OF THE INVENTION

In one embodiment, the present invention provides a rotational atherectomy device with an improved optical reflector which permits one to utilize a single, monofilament optical fiber to transmit light from a light source to the reflector and to return reflected light to a light detector. This rotational atherectomy device includes a prime mover having a prime mover shaft, a flexible drive shaft which is rotatable together with the prime mover, and a handle having a prime mover carriage which carries the prime mover. A generally cylindrical optical reflector is mounted on the prime mover shaft. This reflector has a light-reflective outer surface, a longitudinal bore through which the prime mover shaft extends and a transverse bore extending through the reflector along an axis which is generally perpendicular to the prime mover shaft so that the prime mover shaft obstructs passage of light along the axis of the transverse bore.

In a preferred embodiment, the light source and the light detector are positioned externally of the handle. The proximal end of the optical fiber is permanently secured within the prime mover carriage adjacent the cylindrical reflector such that an axis of a proximal end portion of the optical fiber intermittently becomes generally aligned with the axis of the transverse bore as the cylindrical reflector is rotated together with the prime mover. The distal end of the optical fiber is adapted to be releasably optically coupled to both the light source and the light detector such that the single, monofilament optical fiber both receives light emitted by the light source and returns to the light detector light reflected from the cylindrical reflector. In alternative embodiment, the distal end of the optical fiber is adapted to be releasably receivable within a non-disposable fiber optic connector for releasable optical coupling to a proximal end of a flexible light guide, the flexible light guide having a distal end which is permanently optically coupled to both the light source and the light detector.

The invention also provides a fiber optic connector which includes a housing having proximal and distal ends and defining an elongate internal chamber. A light guide carriage having proximal and distal ends is slidably received within the chamber of the housing, the light guide carriage defining an elongated bore extending between the ends of the carriage. A resilient element biases the carriage proximally with respect to the housing. The connector also includes a flexible light guide, which has a proximal end portion, which is permanently secured within a distal end portion of the elongated bore of the carriage, and at least one optical fiber which may be releasably optically coupled to the flexible light guide. A clamp is carried by the housing proximally of the light guide carriage, the clamp defining a channel through which a distal end portion of the optical fiber may be advanced into a proximal end portion of the elongated bore of the carriage such that the optical fiber is optically coupled to the flexible light guide. This clamp is selectively moveable between an open position, wherein the optical fiber may be moved freely along the channel of the clamp, and a closed position, wherein the clamp prevents free movement of the optical fiber, the clamp moving from its open position to its closed position in response to a clamp actuating signal. A position detector is associated with one of the housing and the carriage and is adapted to generate the clamp actuating signal upon detecting a predetermined change in position of the carriage with respect to the housing.

In another embodiment, the invention provides an optical tachometer for an atherectomy device. This optical tachometer includes at least one optical reflector rotatable together with a shaft of a prime mover; at least one optical fiber having a proximal end which is permanently secured within a prime mover carriage adjacent to the optical reflector; and a fiber optic connector. This fiber optic connector has a housing having proximal and distal ends and defining an elongate internal chamber. A light guide carriage having proximal and distal ends is slidably received within the chamber of the housing, the light guide carriage defining an elongated bore extending between the ends of the carriage. A length of a flexible light guide is permanently received within a distal end portion of the bore. A clamp is carried by the housing proximally of the light guide carriage, the clamp defining a channel through which a distal end portion of the optical fiber may be advanced into a proximal end portion of the elongated bore of the carriage such that the optical fiber is optically coupled to the flexible light guide. This clamp is selectively moveable between an open position, wherein the optical fiber may be moved freely along the channel of the clamp, and a closed position, wherein the clamp prevents free movement of the optical fiber, the clamp moving from its open position to its closed position in response to a clamp actuating signal. A position detector is associated with one of the housing and the carriage and is adapted to generate the clamp actuating signal upon detecting a predetermined change in position of the carriage with respect to the housing.

The invention also provides a rotational atherectomy device which may utilize a single source of compressed gas to drive a prime mover and to actuate a pneumatic clamp. The rotational atherectomy device has a handle with a prime mover carriage which carries the gas driven prime mover. The prime mover is operatively connected to the source of compressed gas. A flexible drive shaft and at least one optical reflector are rotatable together with the prime mover. A pneumatic clamp is operatively connected to the same source of compressed gas which is driving the prime mover. An optical fiber has a proximal end, which is secured within the prime mover carriage adjacent the optical reflector, and a distal end portion which is adapted to be releasably retained by the pneumatic clamp. A light source and a light detector are positioned externally of the handle and are adapted to be optically coupled to the optical fiber when the optical fiber is retained by the pneumatic clamp.

DETAILED DESCRIPTION OF THE PREFERRED EMBODIMENTS

Figure 1:
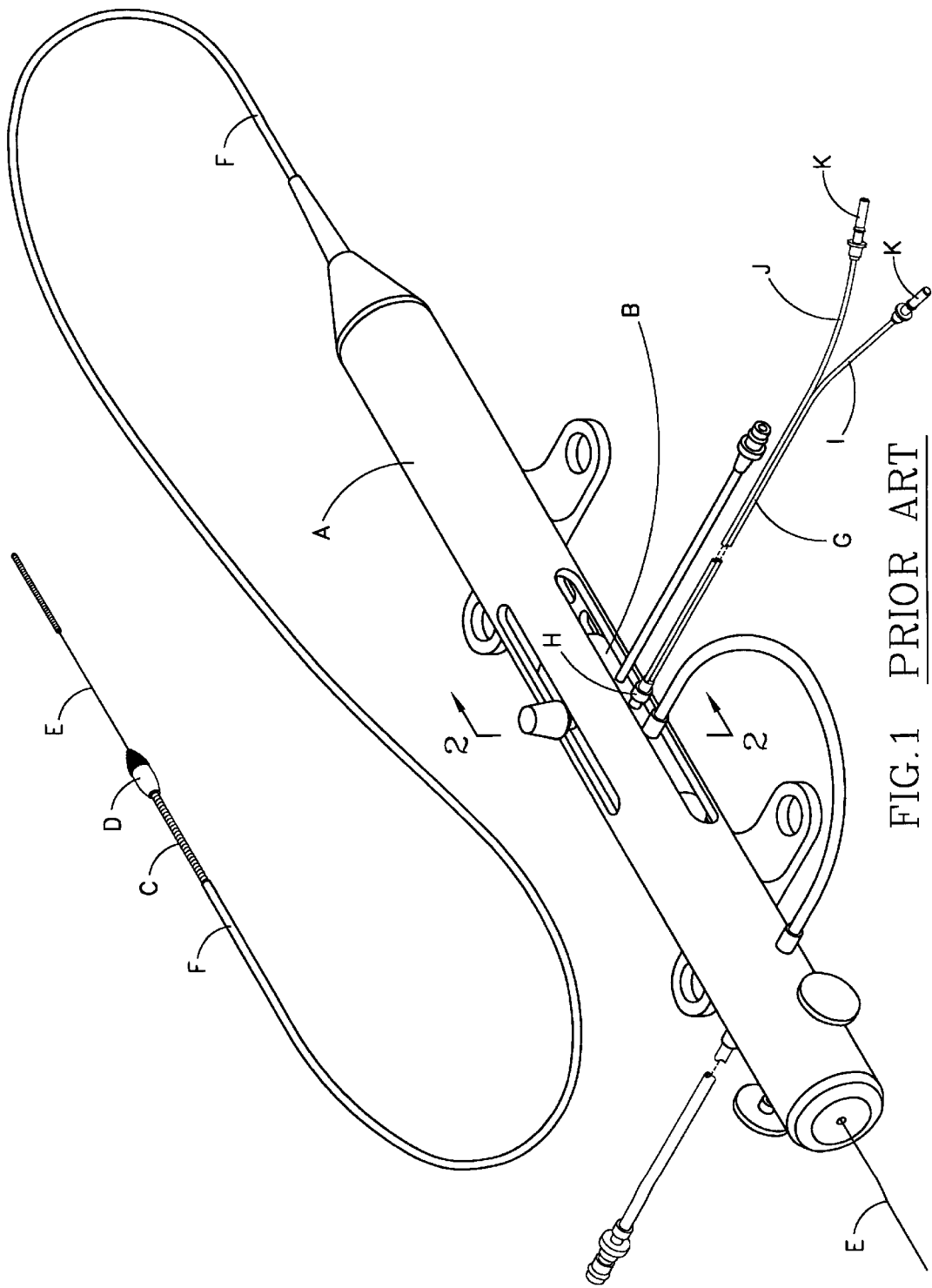
FIG. 1 is a perspective view of the original Rotablator® rotational atherectomy device.
Figure 2:
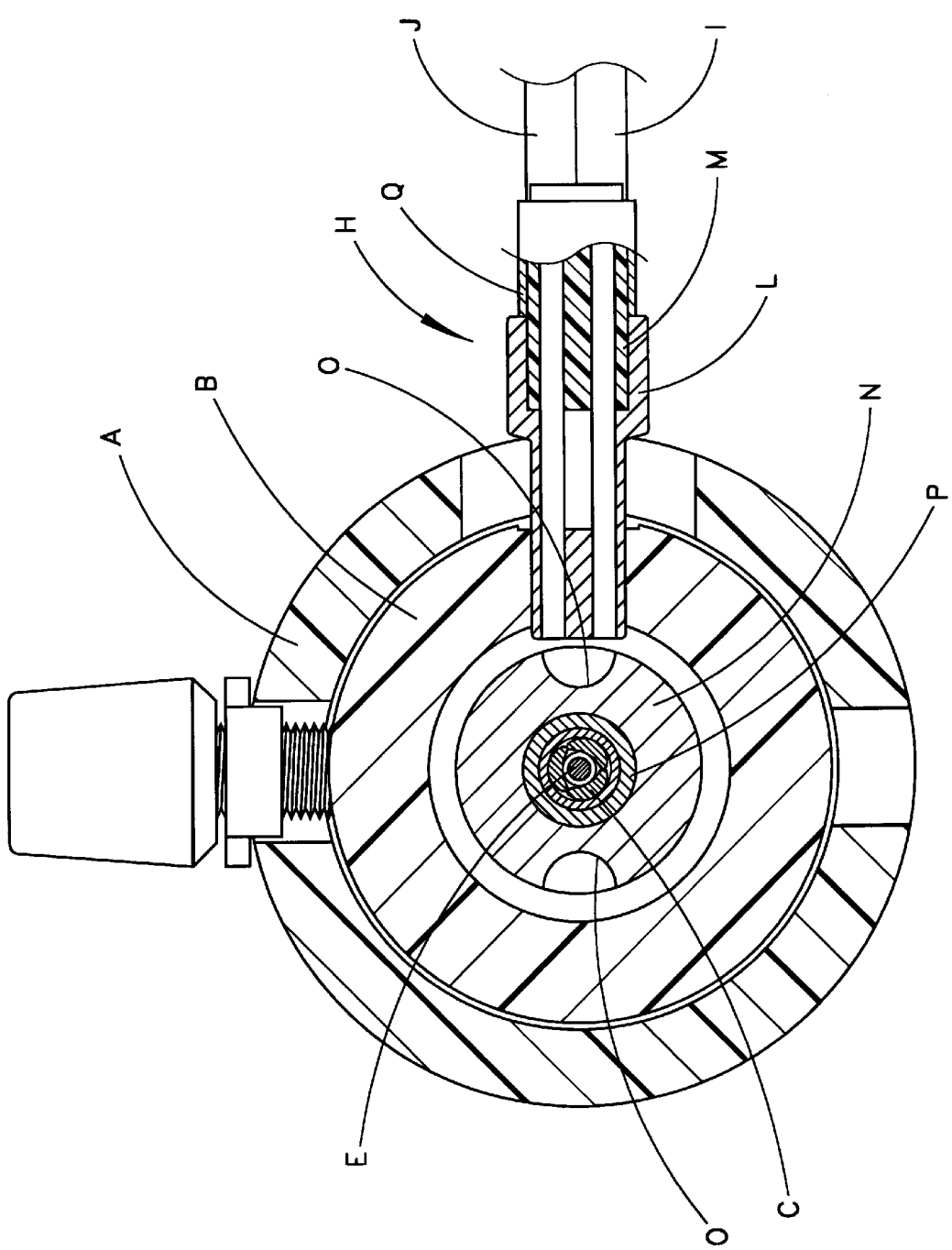
FIG. 2 is a schematic cross sectional view through the optical reflector of the Rotablator® device taken along line 2—2 of FIG. 1.
Figure 3:
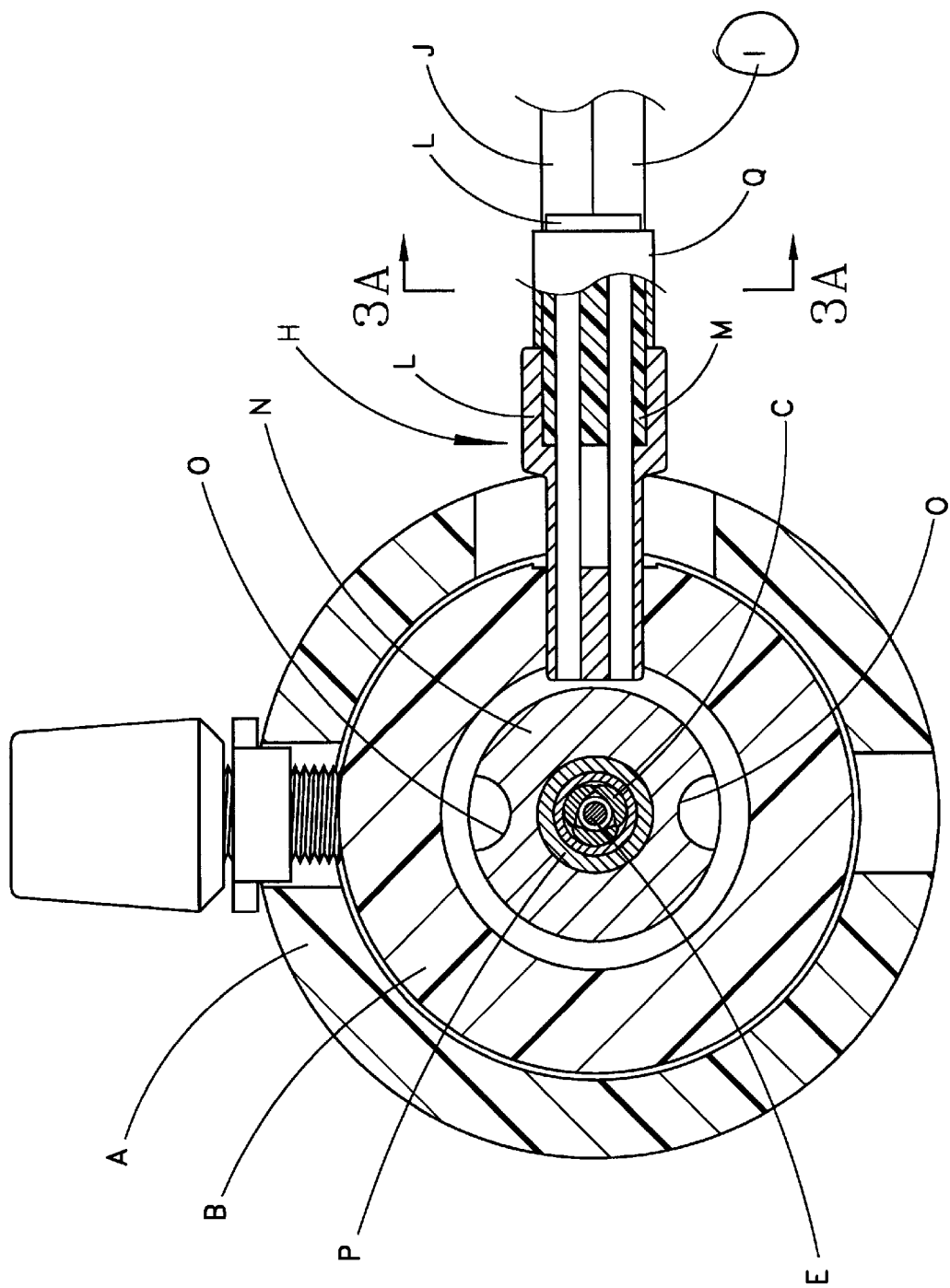
FIG. 3 is a schematic cross sectional view of the Rotablator® device similar to FIG. 2, but showing the optical reflector in a different position.
Figure 3A:
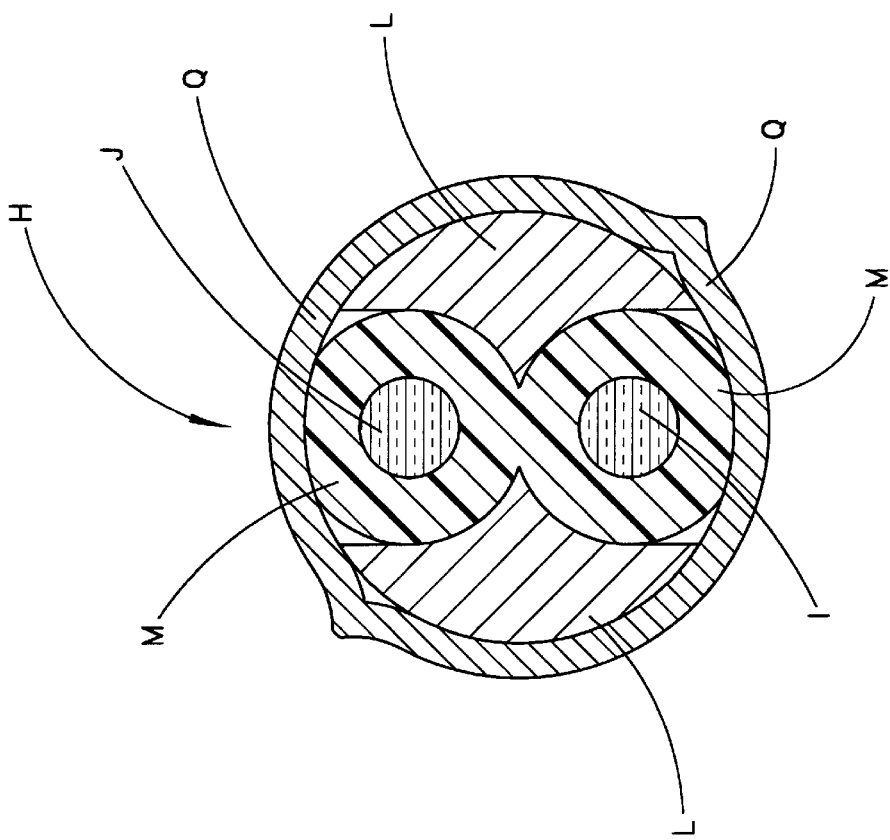
FIG. 3A is a schematic transverse cross sectional view through the dual fiber optic connector of the Rotablator® device taken along line 3A—3A of FIG. 3.
Figure 4:
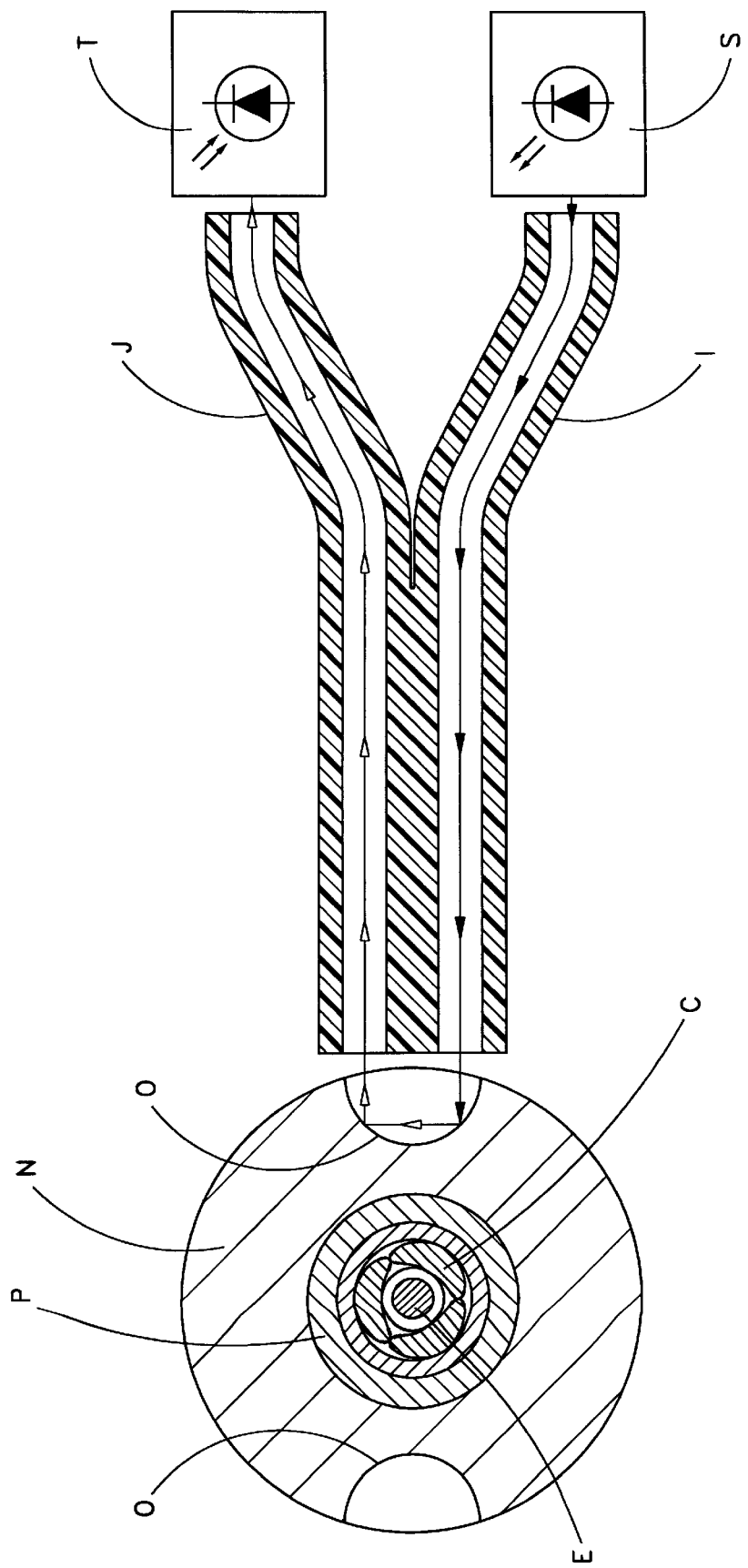
FIG. 4 is a schematic illustration showing how the optical reflector of the Rotablator® device reflects light from one optical fiber into another.
Figure 5:
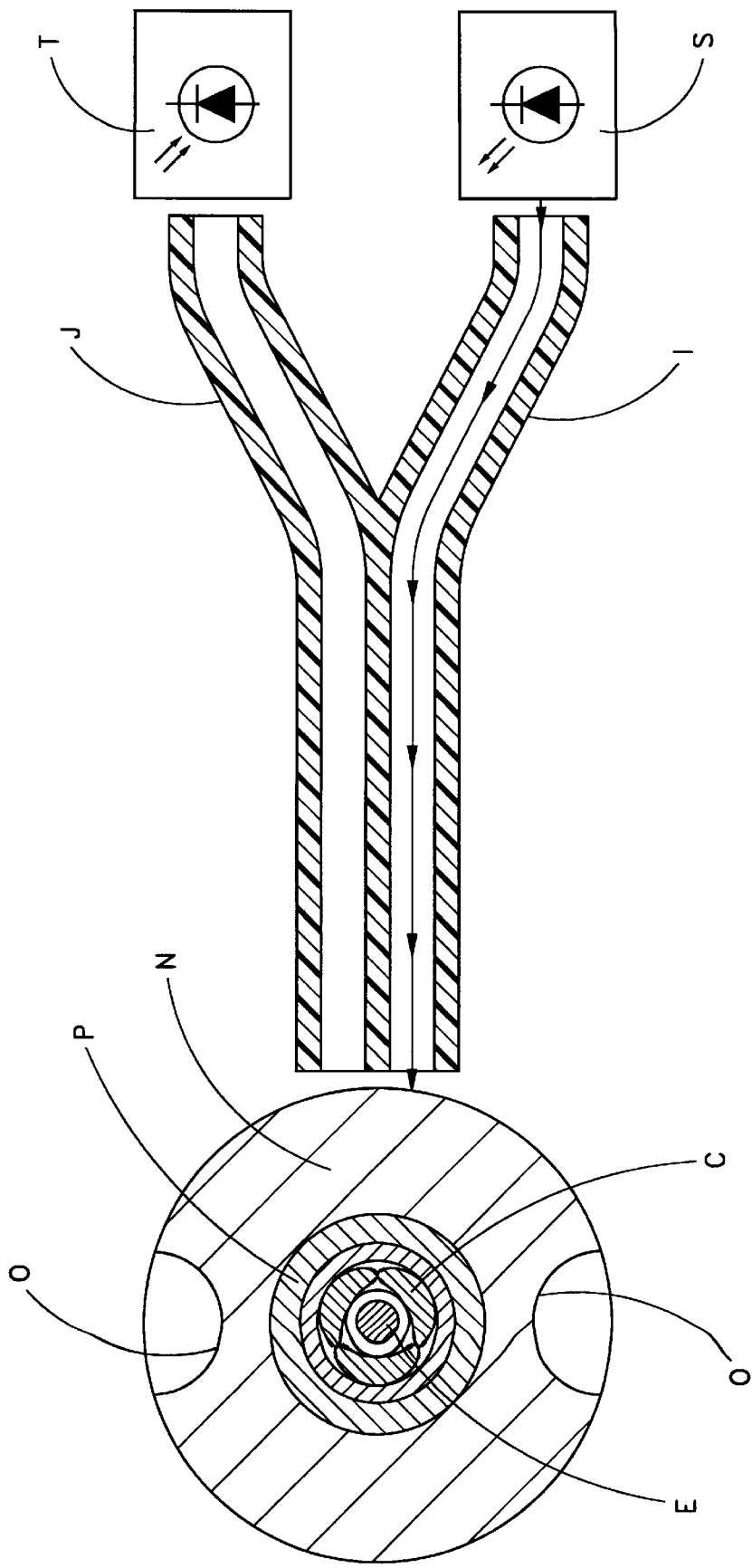
FIG. 5 is a schematic illustration similar to FIG. 4, but showing the optical reflector of the Rotablator® device in a different position wherein it does not reflect light from one optical fiber into the other.

FIGS. 4 and 5 schematically illustrate operation of the optical tachometer of the Rotablator® device shown in FIGS. 1–3 and discussed above. The position of the tachometer rotor N in FIG. 4 corresponds to the position shown in FIG. 2 and the position of the tachometer rotor N in FIG. 5 corresponds to the position shown in FIG. 3. When the tachometer rotor N is in the position shown in FIG. 4, the hemispherical reflective surface O will reflect light from the first fiber optic cable I into the second fiber optic cable J. Light is generated by a light emitting diode S positioned adjacent the distal end of the first fiber optic cable I. During each turn of the rotor N, each hemispherical reflective surface O briefly faces the proximal ends of both optical cables. As illustrated in FIG. 4, when the hemispherical reflective surface O faces the proximal ends of both optical cables, it reflects the light exiting the proximal end of the first fiber optic cable I into the proximal end of the second fiber optic cable J. This reflected light then travels to the distal end of the second fiber optic cable J to illuminate a photodetector T, which generates an electrical signal.

FIG. 5 is a schematic illustration similar to FIG. 4, but shows the tachometer rotor N in a position wherein the exterior surface of the rotor faces the proximal ends of the fiber optic cables I and J. When the rotor is in this position, light exiting the proximal end of the first fiber optic cable I will impinge on the less reflective exterior surface of the rotor. As a consequence of the convex shape and poor reflectivity of this surface, very little light is reflected into the proximal end of the second fiber optic cable J and is transmitted to the photodetector T.

The light emitting diode S is continuously on, so light constantly shines on the rotor N. As the rotor N is rotated, a pulse of reflected light will trigger the photodetector T each time one of the hemispherical reflective surfaces O is properly positioned with respect to the proximal ends of both the first and second fiber optic cables I and J. Hence, the number of light pulses detected by the photodetector T in a given time corresponds to the number of hemispherical reflective surfaces O which pass the proximal ends of the fiber optic cables I and J. With two hemispherical reflective surfaces O on the tachometer rotor N, the number of light pulses detected by the photodetector T per minute corresponds to twice the rotational speed of the prime mover shaft P in revolutions per minute (rpm). Accordingly, in order to determine the rotational speed of the turbine shaft in rpm, the number of light pulses detected by the photodetector T is counted over a period of time, normalized to a minute, and that number is divided by the number of hemispherical reflective surfaces O (in this case 2) to derive the speed of the prime mover shaft P in rpm.

It is important to note that if the dual fiber optic connector (H in FIGS. 2 and 3) does not precisely position the proximal ends of the fiber optic cables I and J with respect to each other and with respect to each hemispherical reflective surface O, then the amount of the light reflected by the hemispherical reflective surface into the proximal end of the second fiber optic cable J likely will be inadequate for the photodetector T to generate an adequate electrical pulse. As a consequence, accurate tracking of the rotational speed of the prime mover shaft P may be impossible. To avoid this problem, the dual fiber optic connector H must rather precisely fix the positions of each of the first and second fiber optic cables I and J in the prime mover carriage B. This requires that the connector H be manufactured to fairly close tolerances, driving up the cost of the disposable Rotablator® device.

The precision with which the hemispherical reflective surface O is machined or formed is also critical in ensuring that the amount of light reflected into the proximal end of the second fiber optic cable J is sufficient for the photodetector T to generate an adequate electrical pulse. In addition, the Rotablator® device operates at rotational speeds of 140,000 rpm or more. At such speeds, even slight imbalances in the weight distribution of the rotor N about its axis of rotation can cause significant problems. Hence, the hemispherical reflective surfaces O must be positioned exactly diametrically opposite one another to ensure that the weight of the rotor is properly balanced. The close tolerances necessary to produce such a tachometer rotor N contribute to the cost of manufacturing the Rotablator® device.

Figure 6:
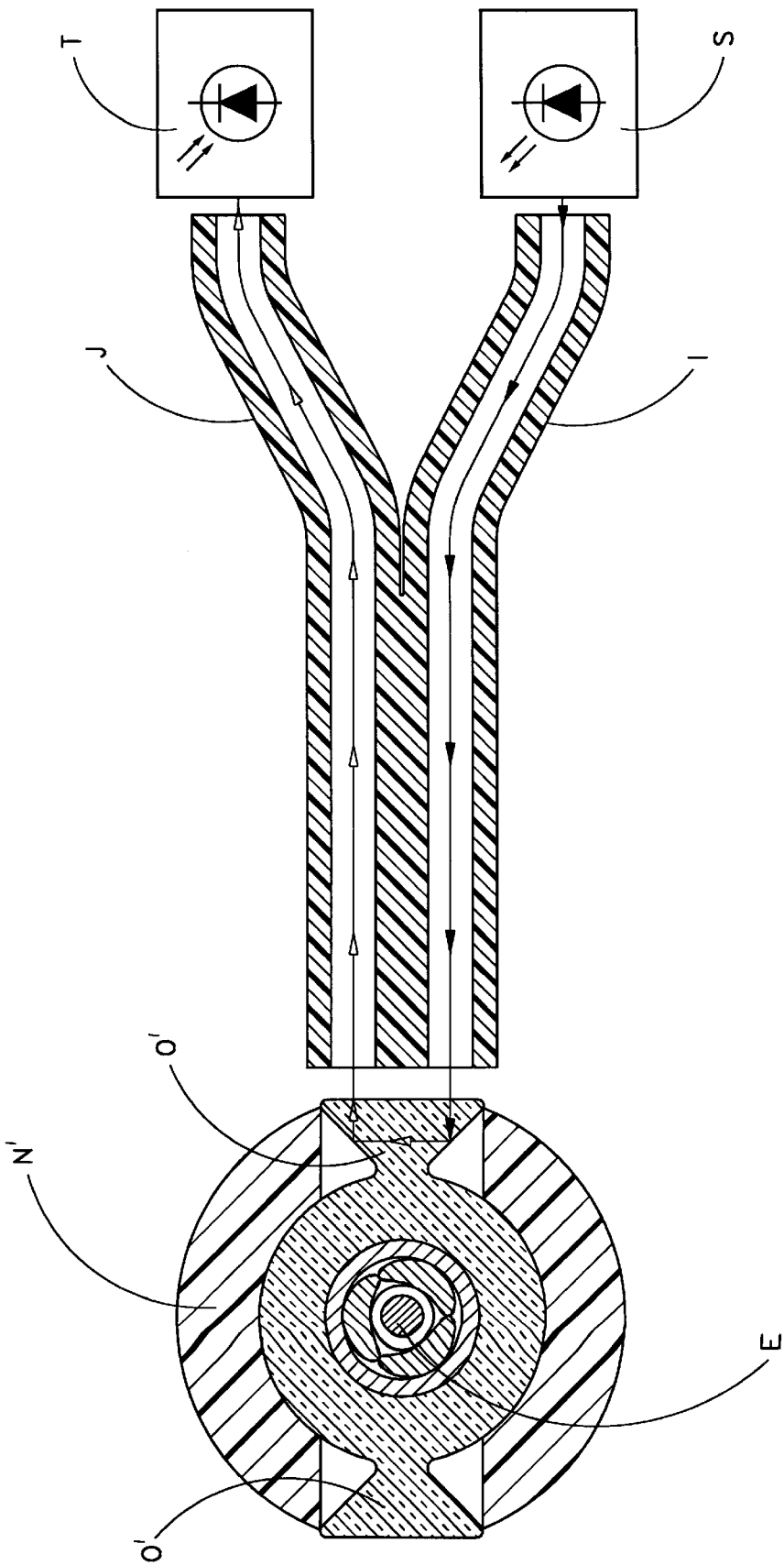
FIG. 6 is a schematic illustration similar to FIG. 2, but showing how an alternative optical reflector used in the Rotablator® RotaLink™ System reflects light from one optical fiber into another.

FIG. 6 is a schematic illustration similar to FIG. 4, but showing an alternative tachometer rotor N' used in a more recent commercial embodiment of the Rotablator® RotaLink™ System. Rather than employing a pair of hemispherical reflective surfaces O machined or otherwise formed in the rotor N, this rotor N' carries a pair of prisms O'. These prisms are internally reflective, serving to direct light from the proximal end of the first fiber optic cable I to the proximal end of the second fiber optic cable J. The two prisms O' can be formed as part of a single element, making it easier to produce a balanced rotor. However, the use of reflective prisms requires that the proximal end portions of the fiber optic cables I and J lie in a plane which is perpendicular to the axis of rotation of the tachometer rotor N'. To satisfy this requirement, the rotational orientation of the dual fiber optic connector (H in FIGS. 2 and 3) with respect to the prime mover carriage B must be carefully controlled.

Figure 7:
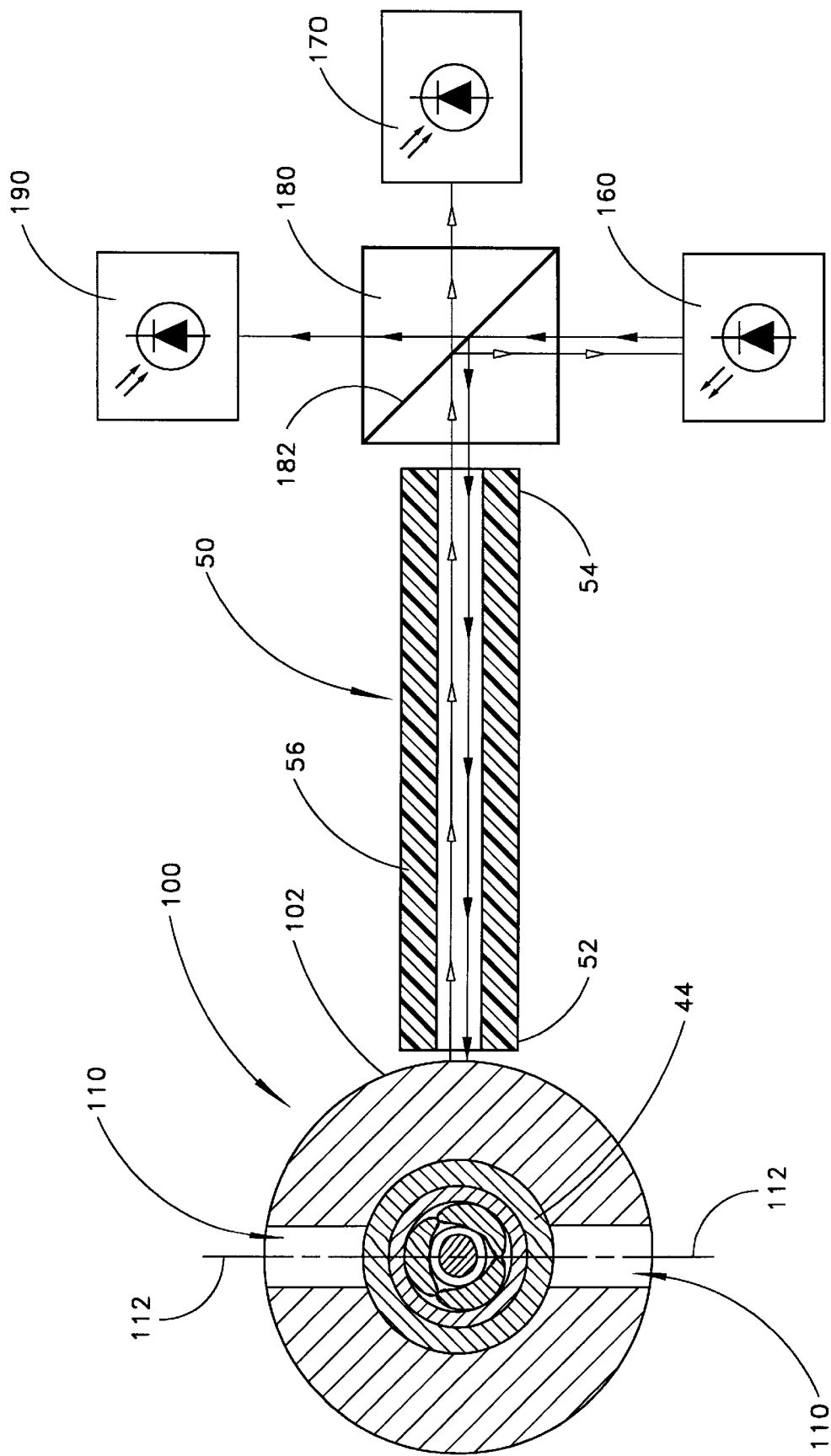
FIG. 7 is a schematic illustration showing how an improved optical reflector of the invention permits one to utilize a single, monofilament optical fiber to transmit light from a light source to the reflector and to return reflected light to a light detector.
Figure 8:
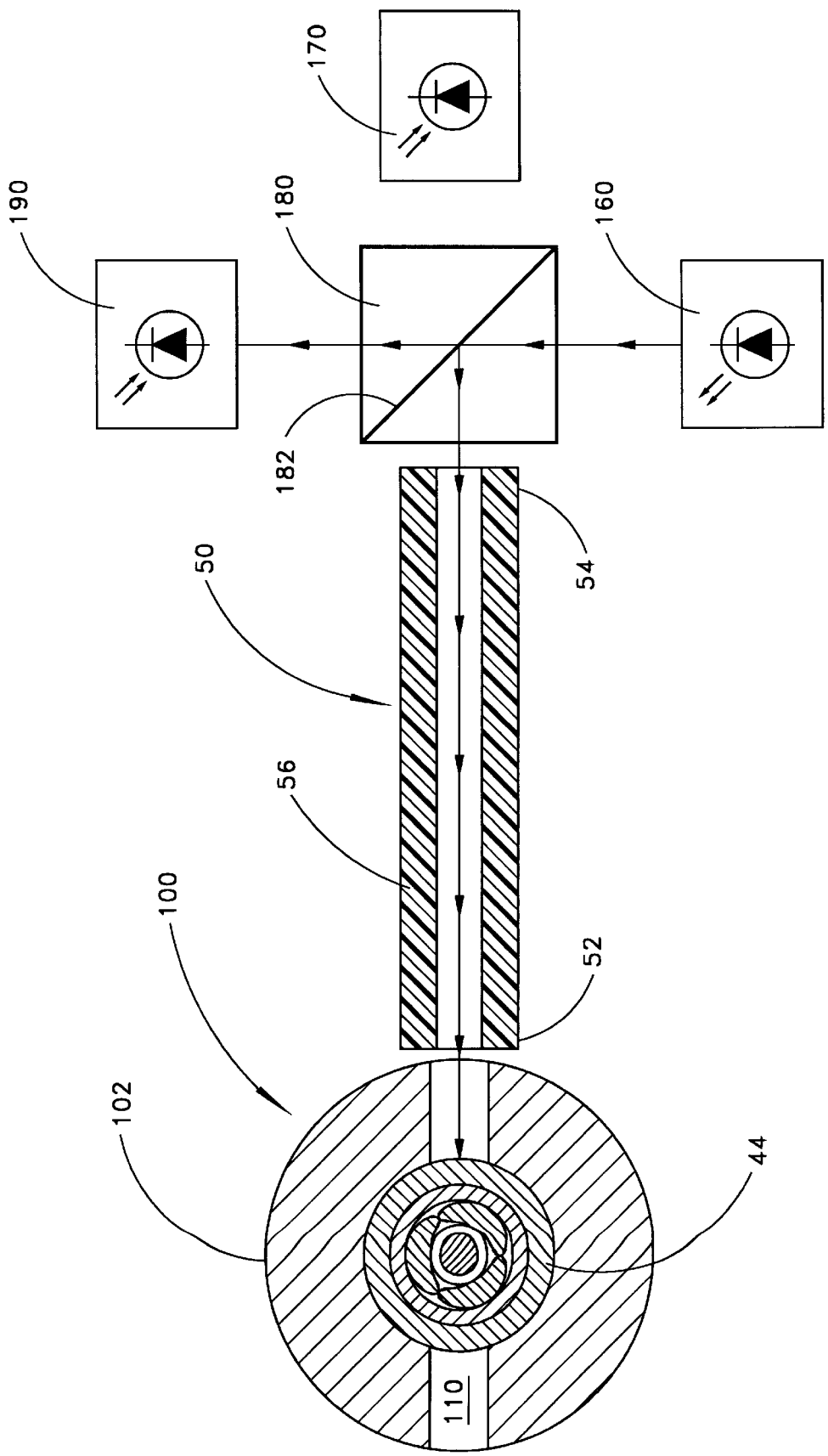
FIG. 8 is a schematic illustration similar to FIG. 7, but showing the optical reflector in a.different position wherein it does not reflect light back into the optical fiber.

FIGS. 7 and 8 schematically illustrate operation of a rotational atherectomy device having an improved optical tachometer in accordance with one embodiment of the invention. The overall structure of the rotational atherectomy device is described more fully below in connection with FIGS. 11–13.

Figure 10:
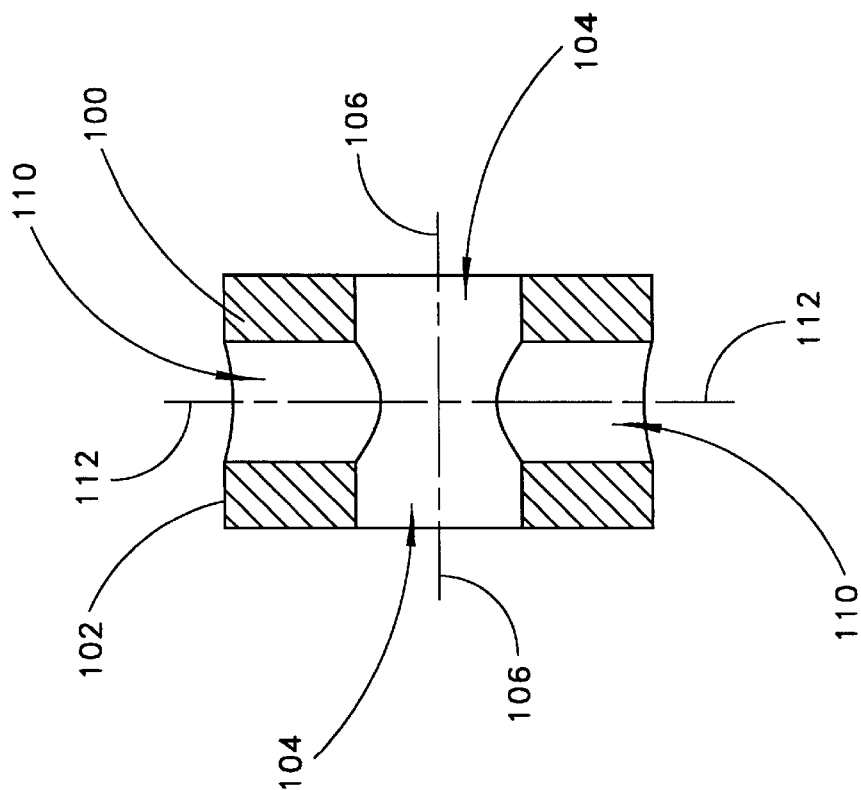
FIG. 10 is a cross sectional view of the optical reflector taken along line 10—10 of FIG. 9.

As shown in FIGS. 7 and 8, the rotational atherectomy device includes an optical reflector 100 which is mounted on a prime mover shaft 44 for rotation together with a prime mover. This optical reflector 100 (separately illustrated in FIGS. 9 and 10) is generally cylindrical in shape and has a convex, reflective outer surface 102. A transverse bore 110 extends through the optical reflector along an axis 112 which is perpendicular to the longitudinal axis (106 in FIG. 10) of the optical reflector. The optical reflector also has a longitudinal bore 104 which extends along the longitudinal axis 106 of the optical reflector. The prime mover shaft 44 extends through and is fixed within this longitudinal bore 104. As a consequence, the axis 112 of the transverse bore 110 is generally perpendicular to the prime mover shaft 44 and the prime mover shaft obstructs passage of light along the axis 112 of the transverse bore 110.

The rotational atherectomy device of FIGS. 7 and 8 also includes a single, monofilament optical fiber 50. This optical fiber includes a protective plastic jacket 56. A proximal end portion 52 of the optical fiber 50 is positioned adjacent the optical reflector 100 and a distal end portion 54 of the optical fiber is adapted to be releasably optically coupled to both a light source 160 and a light detector 170 via a beam splitter 180. Any other suitable fiber optic coupler may be used instead of the beam splitter 180. The light source 160, the light detector 170 and the beam splitter 180 desirably are part of a non-disposable control module positioned externally of the handle of the rotational atherectomy device. As shown in FIGS. 7 and 8, a partially reflective surface 182 of the beam splitter 180 directs at least a portion of the light from the light source 160 into the distal end portion 54 of the optical fiber 50. The light then follows the optical fiber and exits the proximal end of the fiber 50 adjacent the optical reflector 100. (This light path is illustrated by solid black arrows in FIGS. 7 and 8.)

When the reflective outer surface 102 of the optical reflector 100 is positioned adjacent the proximal end of the optical fiber 50, light exiting the proximal end of the optical fiber will be reflected back toward the same optical fiber. Ideally, the proximal end portion 52 of the optical fiber is oriented along an axis which is perpendicular to the longitudinal axis 106 of the optical reflector 100. This will maximize the amount of light that reflects back into the optical fiber 50. Optical reflectors 100 made of stainless steel or aluminum have been used successfully. Preferably, the reflective outer surface 102 of the optical reflector 100 is polished.

As illustrated by phantom arrows in FIG. 7, the light reflected by the optical reflector 100 into the optical fiber 50 then follows a path along the optical fiber 50 and exits the distal end portion 54 of the optical fiber. The beam splitter 180 will then direct at least a portion of the reflected light to the light detector 170, which will generate a relatively long electrical pulse. As a consequence, the same single, monofilament optical fiber 50 can both receive light emitted by the light source 160 and return to the light detector 170 light reflected from the optical reflector 100.

When the proximal end portion 52 of the optical fiber 50 is generally aligned with the axis 112 of the transverse bore, the light exiting the optical fiber will not strike the reflective surface 102 of the optical reflector. Instead, it will travel down into the transverse bore, striking the prime mover shaft 44. If so desired, this prime mover shaft 44 may be made of a minimally reflective material or provided with a minimally reflective coating. This is not believed to be necessary in most instances, though. The amount of light which is reflected back into the optical fiber 50 by the optical reflector 100 will depend in large part on the proximity of the proximal end of the fiber to the surface of the optical reflector. Although it is desirable to position the proximal end of the optical fiber 50 as close as possible to the reflective outer surface 102 of the optical reflector, an adequate amount of light is reflected back into the optical fiber 50 if the reflective outer surface 102 of the optical reflector is positioned about 100–200 μm away from the polished end of the optical fiber 50. The proximal end of the optical fiber 50 is spaced much farther away from the prime mover shaft 44 than it is from the reflective outer surface 102 of the optical reflector 100. Therefore, very little of the light reflected by the prime mover shaft 44 will enter the proximal end of the optical fiber 50 even if the exterior surface of the prime mover shaft 44 is reflective.

When the optical reflector 100 rotates together with the prime mover shaft, the proximal end portion 52 of the optical fiber 50 will be intermittently aligned with the axis 112 of the transverse bore 110. Desirably, the light source 160 is always on. As a consequence, the reflected light shining on the light detector 170 will vary greatly in intensity as the optical reflector 100 rotates, with practically no light being returned to the light detector 170 when the proximal end portion 54 of the optical fiber is generally aligned with the axis 112 of the transverse bore.

The transverse bore extends entirely through the optical reflector, so it interrupts the reflective outer surface 102 of the optical reflector at two diametrically opposite locations. Thus, the light detector 170 will generate two relatively long electrical pulses for each revolution of the optical reflector 100. As a consequence, the number of relatively long electrical pulses per minute detected by the light detector 170 corresponds to twice the rotational speed of the prime mover shaft 44 in revolutions per minute (rpm). To determine the rotational speed of the prime mover shaft in rpm, the number of electrical pulses generated by the light detector 170 is counted over a period of time, normalized to a minute, and divided by two.

A portion of the light emanating from the light source 160 will pass straight through the beam splitter 180, as suggested in FIGS. 7 and 8. If so desired, this transmitted light can be used to monitor the status of the light source 160. The transmitted light can be monitored either by direct visual inspection or electronically, such as by means of a photodetector 190. If the light source is working properly, then the light transmitted through the beam splitter 180 would be detected by the photodetector 190. If no light were received by the photodetector 190, though, this would be an indication that the light source is malfunctioning. As discussed more fully below in connection with FIGS. 14 and 15, the operator can be warned of this malfunction either by providing a simple status indicator light on a control panel or by electronically generating a warning signal.

Figure 11:
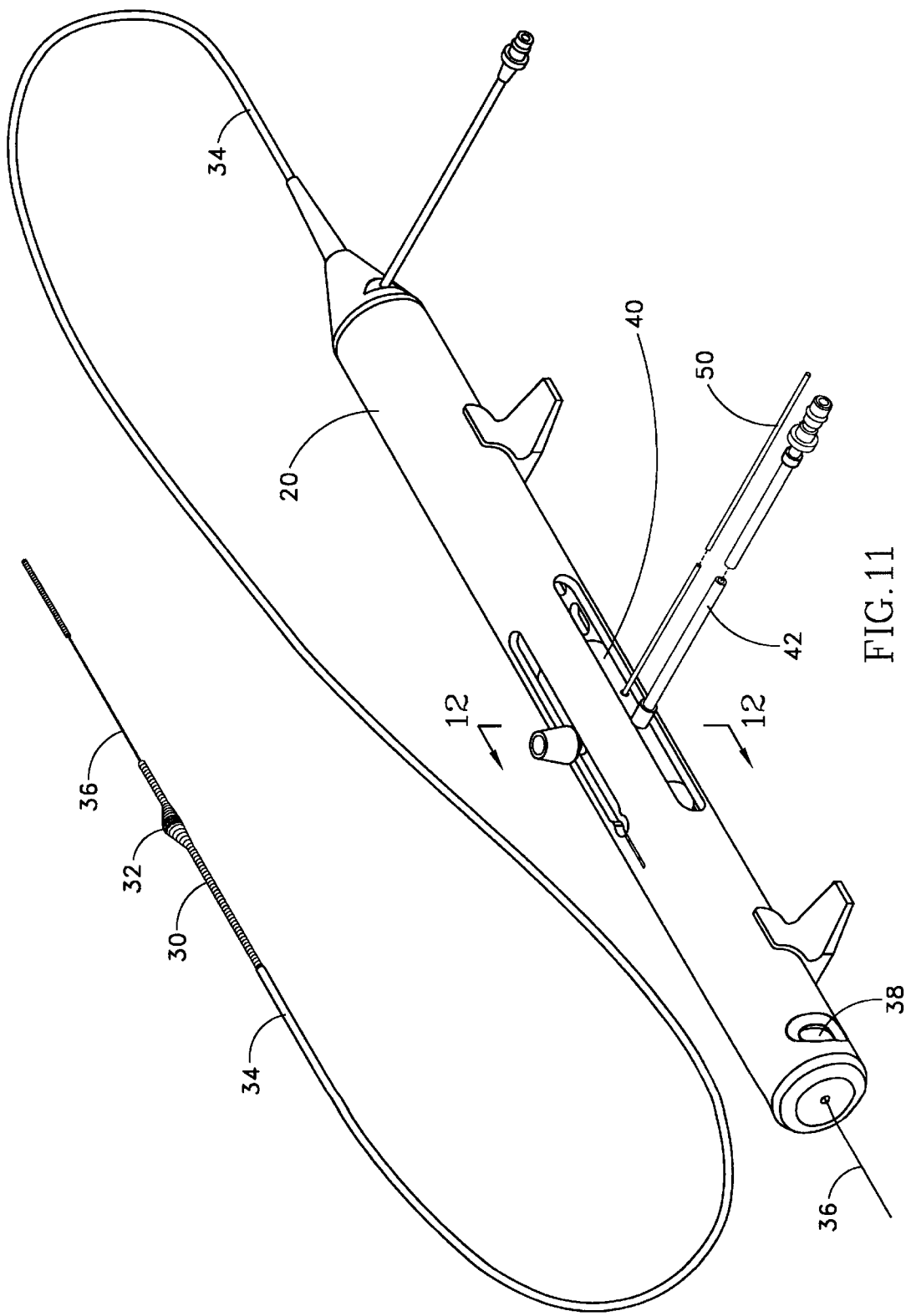
FIG. 11 is a perspective view of one embodiment of a rotational atherectomy device of the invention.

FIG. 11 schematically illustrates a disposable portion of a rotational atherectomy device of the invention. Some of the components of the rotational atherectomy device are similar to the Rotablator® device illustrated in FIG. 1. The rotational atherectomy device shown in FIG. 11 includes an elongate, generally tubular handle 20 which slidably carries a prime mover carriage 40. A compressed gas driven prime mover (not shown) is carried by the prime mover carriage 40. A gas supply line 42 has one end connected to the prime mover carriage 40 and the other end connected to a source of compressed gas (not shown). This gas supply line 42 thereby operatively connects the prime mover to the source of compressed gas. The prime mover is connected to a drive shaft 30 for rotation therewith. The drive shaft 30 is designed to be advanced over and rotated around a guide wire 36. The guide wire is typically held in place using a mechanical guide wire clamp 38 located in the proximal end portion of the handle 20. Most of the length of the drive shaft is disposed inside a catheter 34.

Unlike the Rotablator® device, which includes an abrasive-coated burr D attached to the distal end of the drive shaft C, the drive shaft 30 of a rotational atherectomy device of the present invention includes an eccentric enlarged diameter tissue removal segment 32 which is integrally formed with the drive shaft 30. Such eccentric drive shaft 30 is usually rotated at rotational speeds lower than those employed by the Rotablator® device, with speeds typically not exceeding about 140,000 rpm. It is to be understood, though, that the specific design of the tissue removal segment 32 forms no part of the present invention and a rotational atherectomy device of the invention could employ any type of tissue removal implement which is deemed suitable in the circumstances.

Figure 12:
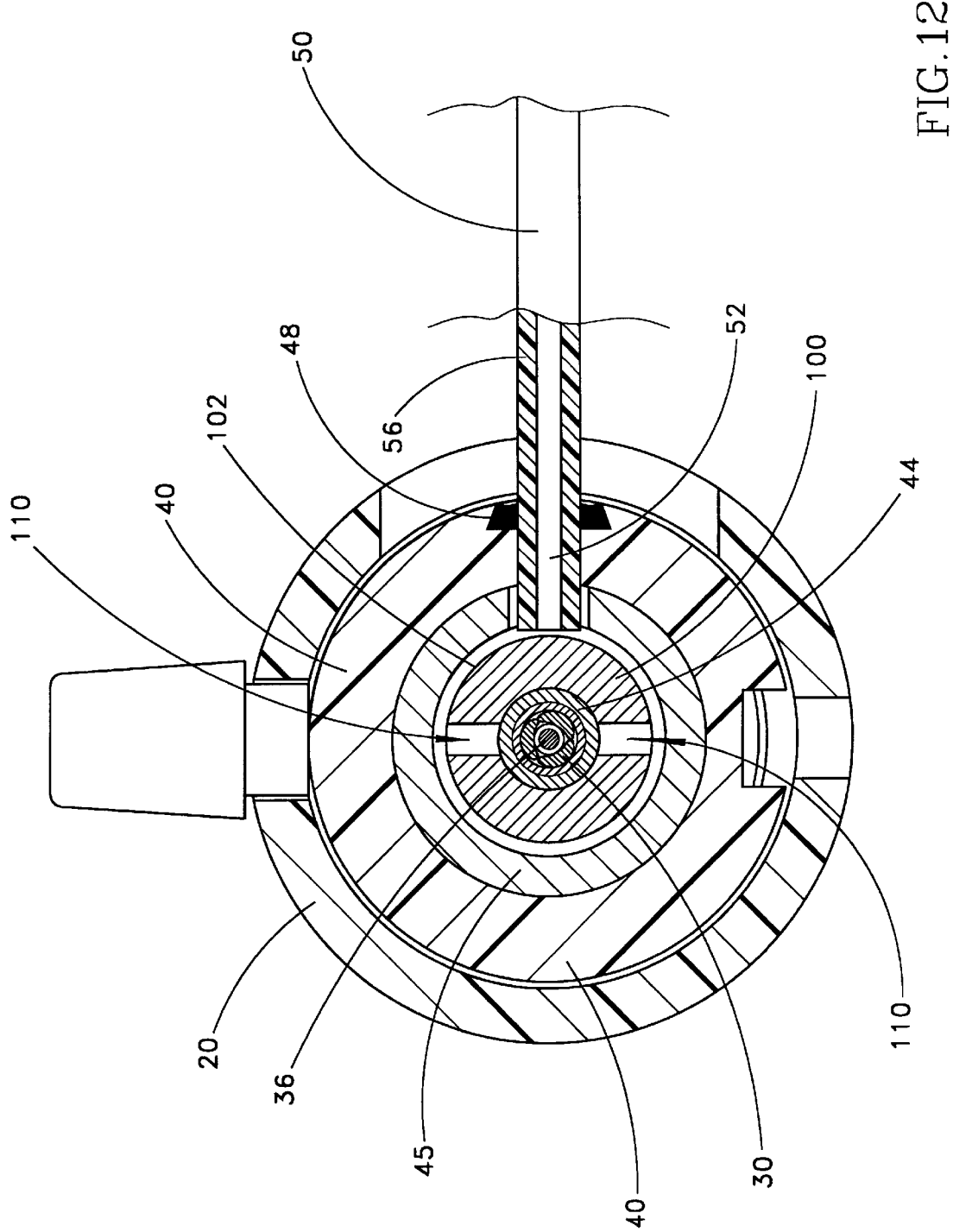
FIG. 12 is a schematic cross sectional view through an optical reflector of the invention taken along line 12—12 of FIG. 11.
Figure 13:
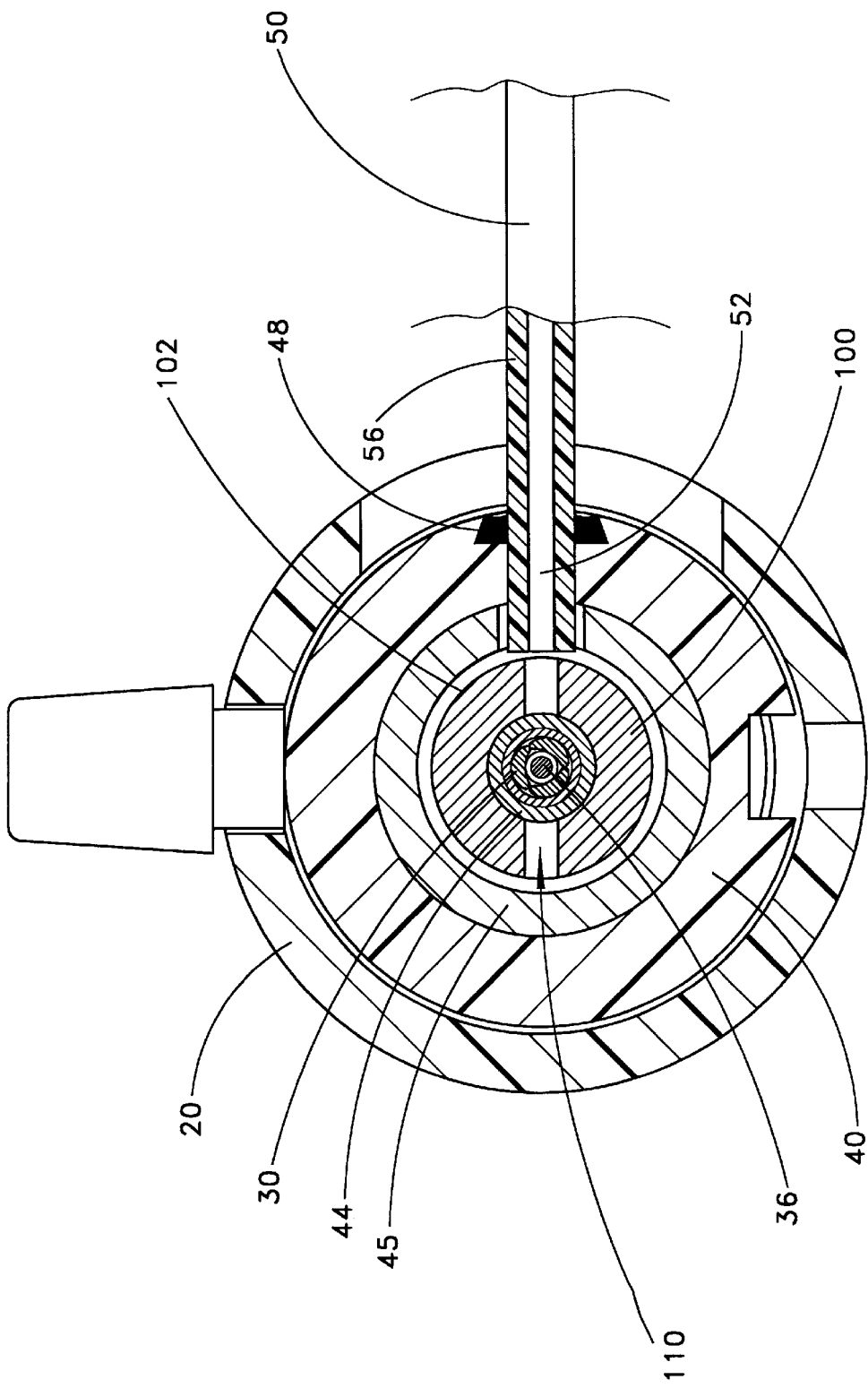
FIG. 13 is a schematic cross sectional view similar to FIG. 12, but showing the optical reflector in a different position.

The rotational atherectomy device shown in FIG. 11 utilizes an optical tachometer having a single, monofilament optical fiber 50. FIGS. 12 and 13 are both schematic cross sectional views of the rotational atherectomy device of FIG. 11 taken along line 12—12 and schematically illustrating how the optical fiber 50 is used in an optical tachometer of the invention. FIGS. 12 and 13 both show an optical reflector 100 of the invention, with the position of the optical reflector in FIG. 12 generally corresponding to that shown schematically in FIG. 7 and the position of the optical reflector in FIG. 13 generally corresponding to that shown schematically in FIG. 8. For purposes of simplicity, the gas supply line 42 and some other structures shown in FIG. 11 have been omitted from FIGS. 12 and 13.

The optical reflector 100 is secured to the prime mover shaft 44 for rotation therewith. The optical reflector 100 is positioned between a pair of bearings (not shown) which support the prime mover shaft 44 within a prime mover housing 45. This prime mover housing 45 is, in turn, carried in the prime mover carriage 40. Optimally, the prime mover carriage 40 is generally cylindrical in shape. Preferably, the generally cylindrical optical reflector 100 is centered on the axis of the prime mover carriage. The optical reflector 100 should be free to rotate within the prime mover housing 45 without any physical contact with the housing, so the outer diameter of the optical reflector 100 is smaller than the inner diameter of the prime mover housing 45.

The proximal end portion 52 of the optical fiber 50 is secured within the prime mover carriage 40. One of the advantages of the illustrated design is that the optical fiber 50 can be secured directly within a bore in the wall of the prime mover carriage 40. (As shown in FIGS. 1–3, a separate fitting H is used to secure the fiber optic cables of the Rotablator® device within the prime mover carriage B.) In the rotational atherectomy device shown in FIGS. 11–13, the plastic optical fiber 50 can be secured in the bore of the prime mover carriage 40 simply by gluing the plastic jacket 56 of the optical fiber 50 in place. If the material of the prime mover carriage 40 does not bond well with glue, the carriage can be provided with a dove-tail slot and the glue 48 can expand to fill that slot, as shown. This will mechanically enhance the bond between the plastic jacket 56 of the optical fiber 50 and the prime mover carriage 40 to keep the proximal end portion 52 of the fiber in place. Optimally, the plastic optical fiber 50 has a plastic jacket 56 made of polyvinyl chloride to enhance bonding with certain commercially available glues, e.g., Loctite™. Such plastic optical fiber is commercially available from Mitsubishi Rayon America, Inc., New York, N.Y., USA under the trade name Super Eska as Product Code SHV-4001.

Care should be taken during assembly to ensure that the proximal end of the optical fiber 50 is properly positioned with respect to the optical reflector 100. If the proximal end of the optical fiber 50 extends too far into the prime mover carriage 40, it could rub against the rotating reflector. If the proximal end of the optical fiber 50 is not inserted far enough into the prime mover carriage 40, then the distance between the optical fiber and the reflective outer surface 102 of the optical reflector may be too great to ensure reliable operation. A jig designed to properly position the proximal end of the optical fiber 50 with respect to the prime mover carriage 40 during assembly should enable one to reliably manufacture this structure.

One other advantage of the illustrated design is that a single, monofilament optical fiber 50 can both receive light emitted by the light source 160 and return to the light detector 170 light reflected from the optical reflector 100. The Rotablator® device shown in FIGS. 1–4 requires two separate fiber optic cables—a first fiber optic cable I to direct light from the light source to the tachometer rotor N and a second fiber optic cable J to carry light reflected by the hemispherical reflective surfaces O to a photodetector T. Obviously, having to provide two separate elements is more expensive than using a single monofilament optical fiber 50.

Because two separate fiber optic cables I and J are used to transmit light to and from the reflective surfaces of the rotor N, the dual fiber optic connector H of the Rotablator® device must be manufactured to fairly tight tolerances to ensure that the light from the proximal end of the first cable I will be properly reflected by the hemispherical reflective surfaces O into the proximal end of the second cable J. In the invention illustrated in FIGS. 7–13, though, there is no need to precisely control the relative positions of three separate elements (two fiber optic cables and one rotor) during assembly. Instead, one need only ensure that the proximal end of the single, monofilament optical fiber 50 be spaced an appropriate distance from the optical reflector 100.

Figure 9:
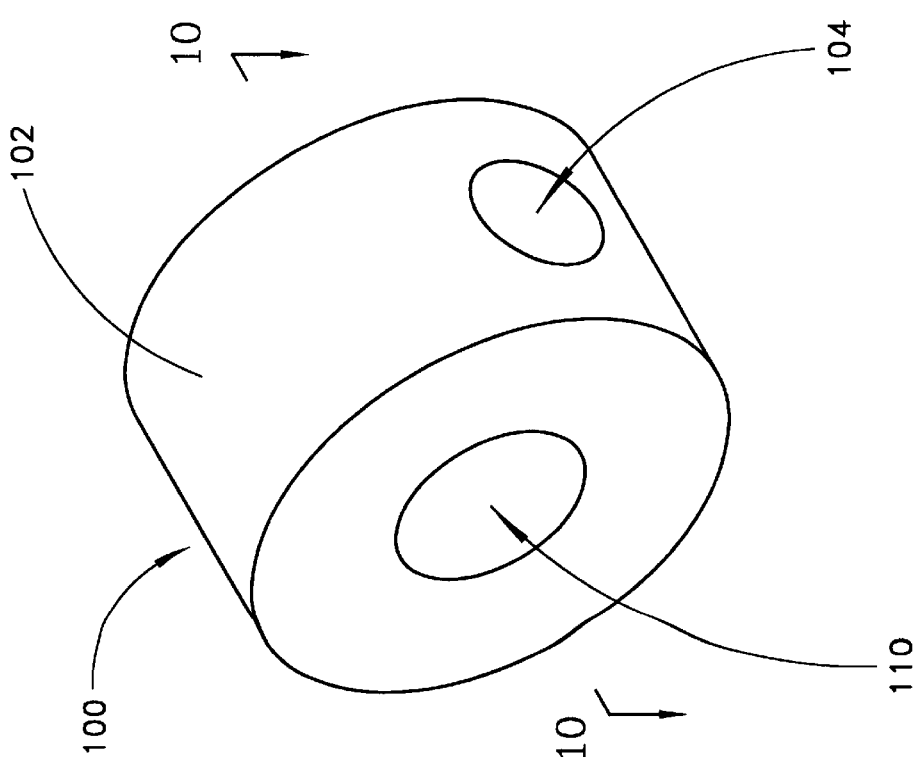
FIG. 9 is a perspective view of the optical reflector schematically illustrated in FIGS. 7 and 8.

The optical reflector 100 of FIGS. 8 and 9 is also much easier to manufacture than either the rotor N of the Rotablator® device shown in FIGS. 2–5 or the alternative rotor N' of the Rotablator® RotaLink™ System shown in FIG. 6. As noted above, the manufacturing tolerances necessary to produce a properly balanced rotor N with suitably shaped hemispherical reflective surfaces O are quite strict. The alternative rotor N' of FIG. 6 is easier to manufacture, but it requires that both fiber optic cables I and J are positioned in a plane which is perpendicular to the axis of rotation of the rotor N'.

The present optical reflector 100 is much easier to manufacture. Instead of having to precisely machine two diametrically opposed hemispherical surfaces to tight tolerances, one can simply drill straight through the body of the optical reflector 100 to form a single transverse bore 110. The size of this transverse bore is not critical—the transverse bore need only be perpendicular to the longitudinal axis 106 of the optical reflector 100. Accordingly, the rotational atherectomy device of the present invention has an optical reflector 100 which is easier and less expensive to manufacture than the tachometer rotor of either of the Rotablator® devices.

Figure 14:
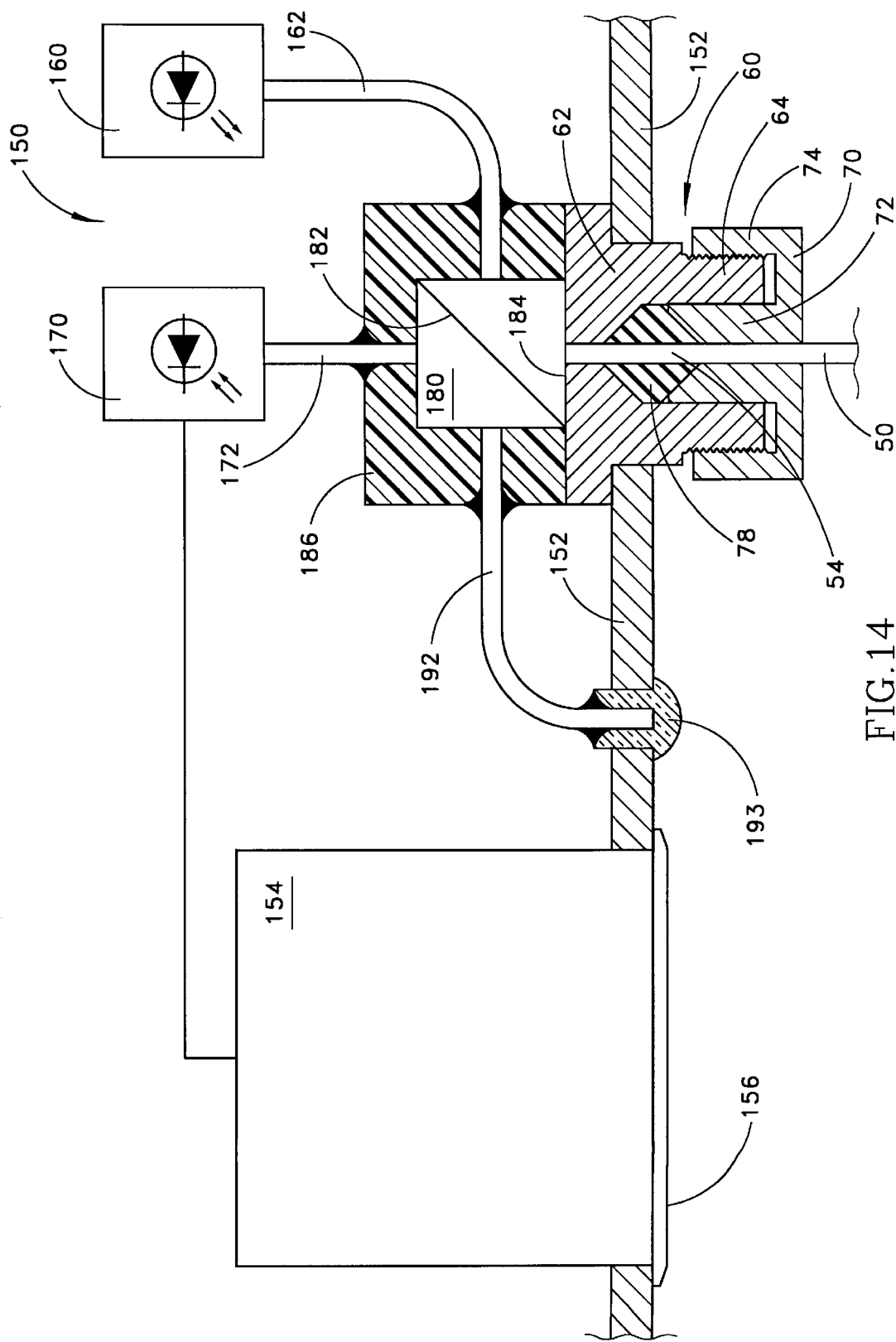
FIG. 14 is a schematic illustration of one optical system of the invention, illustrating how a beam splitter can be utilized to releasably optically couple the single, monofilament optical fiber to both the light source and the light detector.

As noted above, the distal end portion 54 of the optical fiber is adapted to be releasably optically coupled to both a light source 160 and a light detector 170 via the beam splitter 180. The light source 160, the light detector 170 and the beam splitter 180 comprise a non-disposable portion of the optical tachometer of the invention and usually are located within a non-disposable module 150. The non-disposable module 150 may be a stand alone module or it may be a part of a more complex monitoring system which may monitor a number of other parameters of the atherectomy procedure (e.g., the length of each cycle of tissue removal or total time of the procedure). FIG. 14 illustrates one embodiment of such a control module. In one preferred embodiment, the entire portion of the rotational atherectomy device which is shown in FIG. 11 is intended to be discarded after being used for treatment of a single patient; the Rotablator® device is also intended to be a disposable device. The control module 150, though, is not intended to be disposable. Instead, the control module can be reused with multiple handles 20 due to the releasable attachment of the optical fiber 50 to the control module.

If so desired, the control module 150 can be enclosed within a sturdy protective housing. In FIG. 14, the front panel 152 of such a housing is shown. The light source 160, the light detector 170 and the beam splitter 180 may all be enclosed within the housing of the control module. To facilitate releasable optical coupling of the optical fiber 50 to the beam splitter, a fiber optic connector 60 is provided in the front panel 152. (The details of this fiber optic connector 60 are discussed more fully below in connection with FIGS. 16 and 17.) This fiber optic connector is designed to hold the distal end portion 54 of the optical fiber such that the polished distal end of the optical fiber abuts the forward face 184 of the beam splitter 180, thereby optically coupling the fiber to the beam splitter.

A wide variety of commercially available beam splitters may be used as the beam splitter 180 in FIG. 14. One suitable type of beam splitter is a dichroic cube beam splitter, such as is commercially available from Edmund Scientific's Industrial Optics Division, Barrington, N.J., USA. One particular beam splitter which has been found to be suitable for this application is designated as Stock No. P32,600.

Such a beam splitter provides a partially reflective surface 182 defined at the interface of the faces of two prisms. As illustrated in the drawings, this surface 182 is oriented at an angle (typically about 45°) with respect to the beam of light from the light source 160. When light from the light source 160 strikes the partially reflective surface 182, a predetermined percentage of light will be transmitted through the surface 182 and out the opposite face of the cube. The remainder of the light (less transmission losses of the cube) will be reflected at an angle and into the distal end of the optical fiber 50. Light reflected by the optical reflector 100 and carried back to the beam splitter 180 by the optical fiber 50 will also encounter the partially reflective surface 182. Again, a predetermined percentage of light will simply pass straight through the surface 182 and reach the photodetector 170 while the remainder of the light will be reflected at an angle.

Commercially available beam splitters provide different ratios of reflected versus transmitted light. A beam splitter which reflects about the same amount of light as it transmits is believed to be most suitable for use in the optical tachometer of the invention.

An optical fiber 162 may be used to guide the light from the light source 160 to the beam splitter 180. This optical fiber 162 has proximal and distal ends. The proximal end of the optical fiber 162 is permanently optically coupled to the light source. The distal end of the optical fiber 162 is permanently optically coupled to the beam splitter. As more fully described below in connection with FIGS. 16 and 17, the beam splitter 180 may be retained in a mounting block 186. The optical fiber 162 can be joined to the beam splitter by abutting the polished distal end of the fiber 162 against the face of the beam splitter cube and gluing or otherwise affixing the distal end portion of the fiber 162 to the mounting block 186. The light source can be of any known variety. Preferably, the light source comprises a light emitting diode emitting light in the visible range. One light source which has been found to work well is a plastic fiber optic emitter commercially available from Siemens Components, Inc. Optoelectronics Division of Cupertino, Calif., USA as Part No. SFH756V.

The light detector 170 can be coupled to the beam splitter 180 by an optical fiber 172 in much the same fashion as the light source 160 is coupled to the beam splitter by the optical fiber 162. The optical fibers 172 and 162 should be attached to adjacent faces of the beam splitter 180. The light detector 170 should be capable of detecting light of the wavelength (s) emitted by the light source and generating an electrical signal when the intensity of the light shining on the detector meets or exceeds a predetermined threshold value. For example, the light detector may comprise a photodiode detector or a phototransistor. One light detector which has been found to work well with the Siemens SFH756V plastic fiber optic emitter mentioned above is a plastic fiber optic photodiode detector SFH250V, also available from Siemens Components, Inc.

The electrical signal from the light detector 170 can be delivered to a signal processor 154. This signal processor should be adapted to process the signal from the light detector to determine the rotational speed of the prime mover. The processor 154 can display this rotational speed on a display 156 mounted on the front panel 152 of the housing of the control module 150. The processor may also be designed to warn the user of any detected problems or even to take necessary emergency measures, such as to terminate air supply to the prime mover if the rotational speed drops too far or too quickly.

In the illustrated embodiment, a portion of the light from the light source 160 is transmitted straight through the beam splitter and this transmitted light can be used to monitor the status of the light source. FIG. 14 illustrates a very simple way of displaying this status to the operator using a status-indicating optical fiber 192. The status-indicating optical fiber 192 has proximal and distal ends. The polished proximal end of the status-indicating optical fiber abuts the face of the beam splitter opposite the distal end of the optical fiber 162, which brings light from the light source 160. The proximal end portion of the status-indicating optical fiber 192 should be optically aligned with the distal end portion of the optical fiber 162 in order to transmit light from the optical fiber 162 into the status-indicating optical fiber 192.

The distal end of the status-indicating optical fiber 192 can be viewed by an operator through a hole in the front panel 152 of the control module. If so desired, the distal end of the status-indicating optical fiber 192 can be attached to a plastic lens 193 which is, in turn, attached to the front panel 152. Such a plastic lens can make the light from the status-indicating optical fiber more visible.

Figure 15:
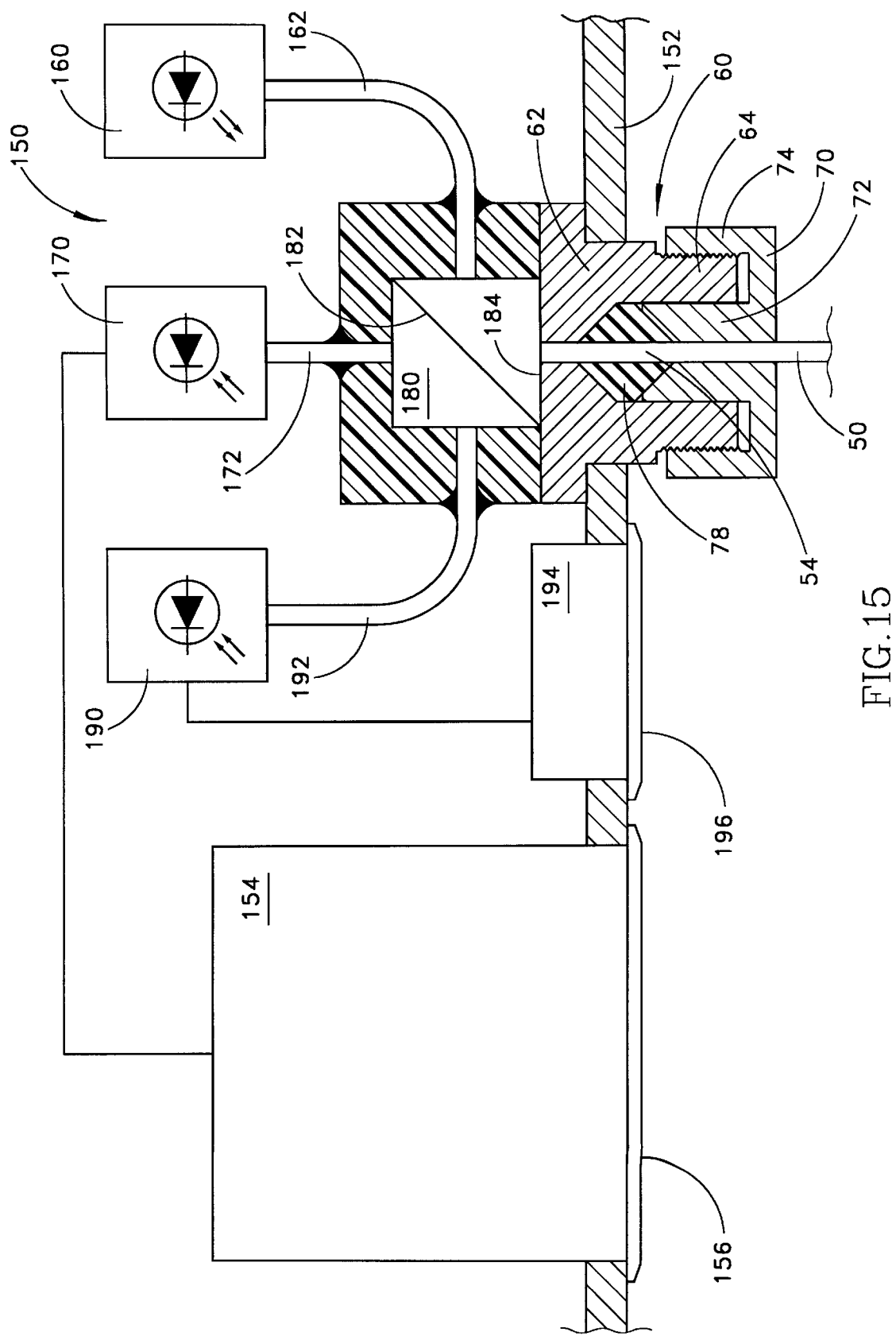
FIG. 15 is a schematic illustration, similar to FIG. 14, but depicting an optical system with an additional light detector to monitor the status of the light source.

FIG. 15 shows an alternative embodiment of the control module 150. The only difference between the control module of FIG. 15 and that shown in FIG. 14 is the manner in which the status of the light source 160 is displayed to the operator. In the embodiment of FIG. 15, the status is displayed with the benefit of a second light detector 190. This light detector 190 may comprise a photodiode of the same model as the light detector 170, but a different, less expensive photodiode (or phototransistor) may be used instead. The electrical signal from the second light detector 190 can be delivered to a status processor 194 which will display the status of the light source on a display 196 which is mounted on the front panel 152 of the control module 150.

Figure 16:
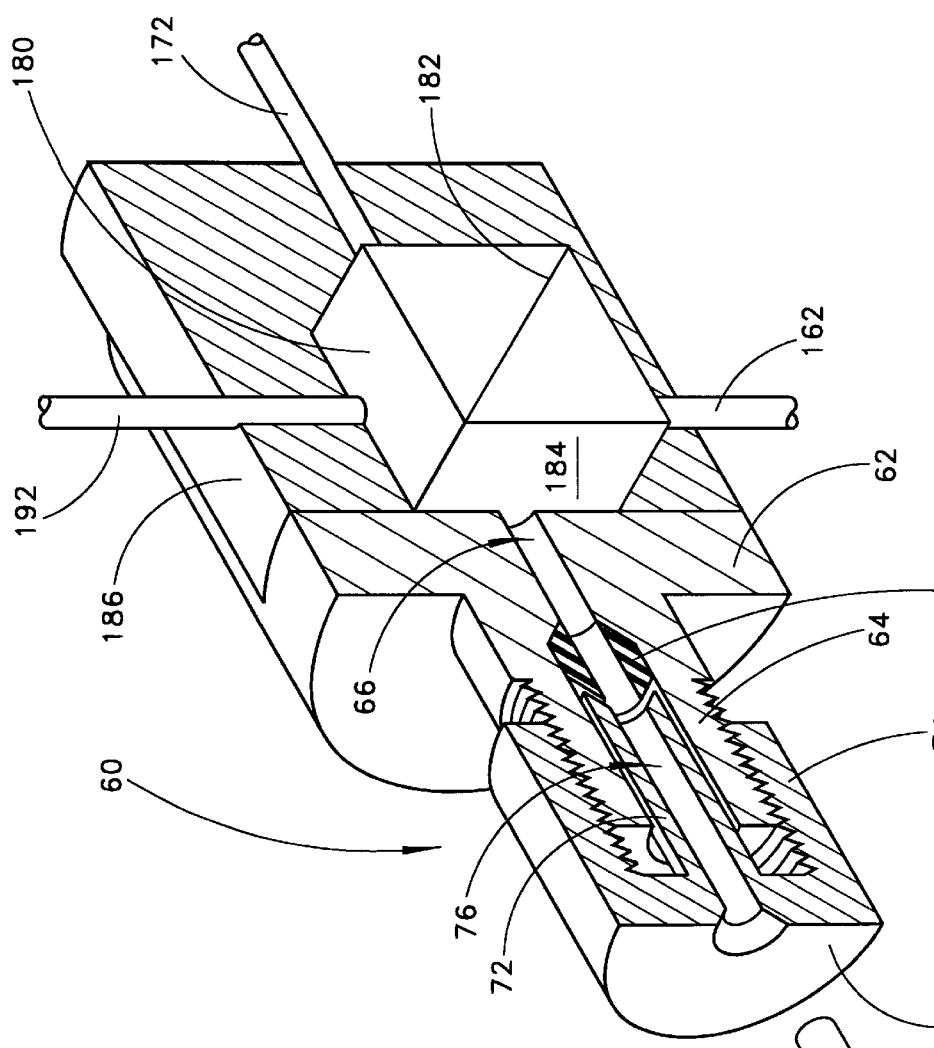
FIG. 16 is a simplified perspective, cross sectional view of the fiber optic connector schematically shown in FIGS. 14 and 15.
Figure 16:
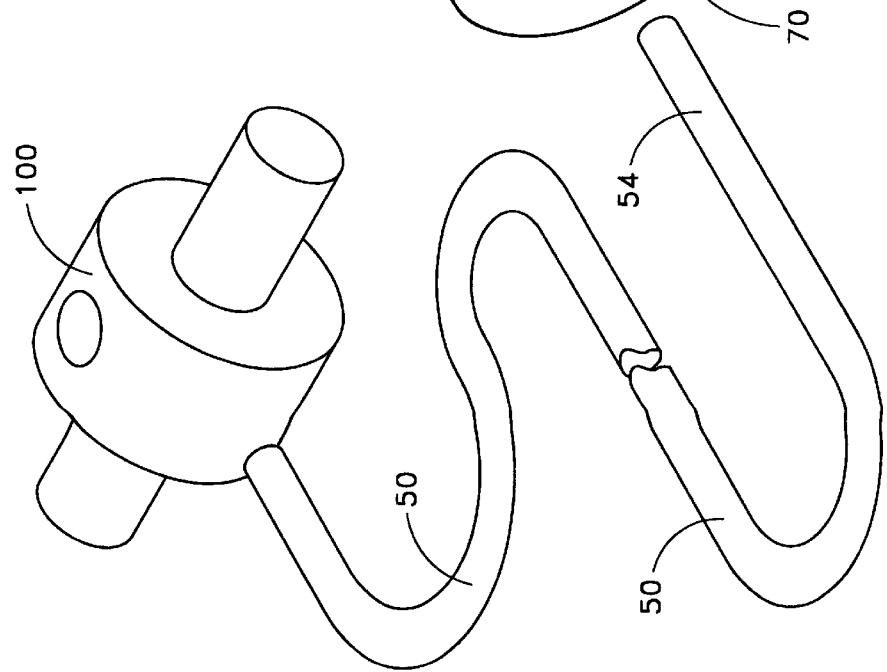
Figure 17:
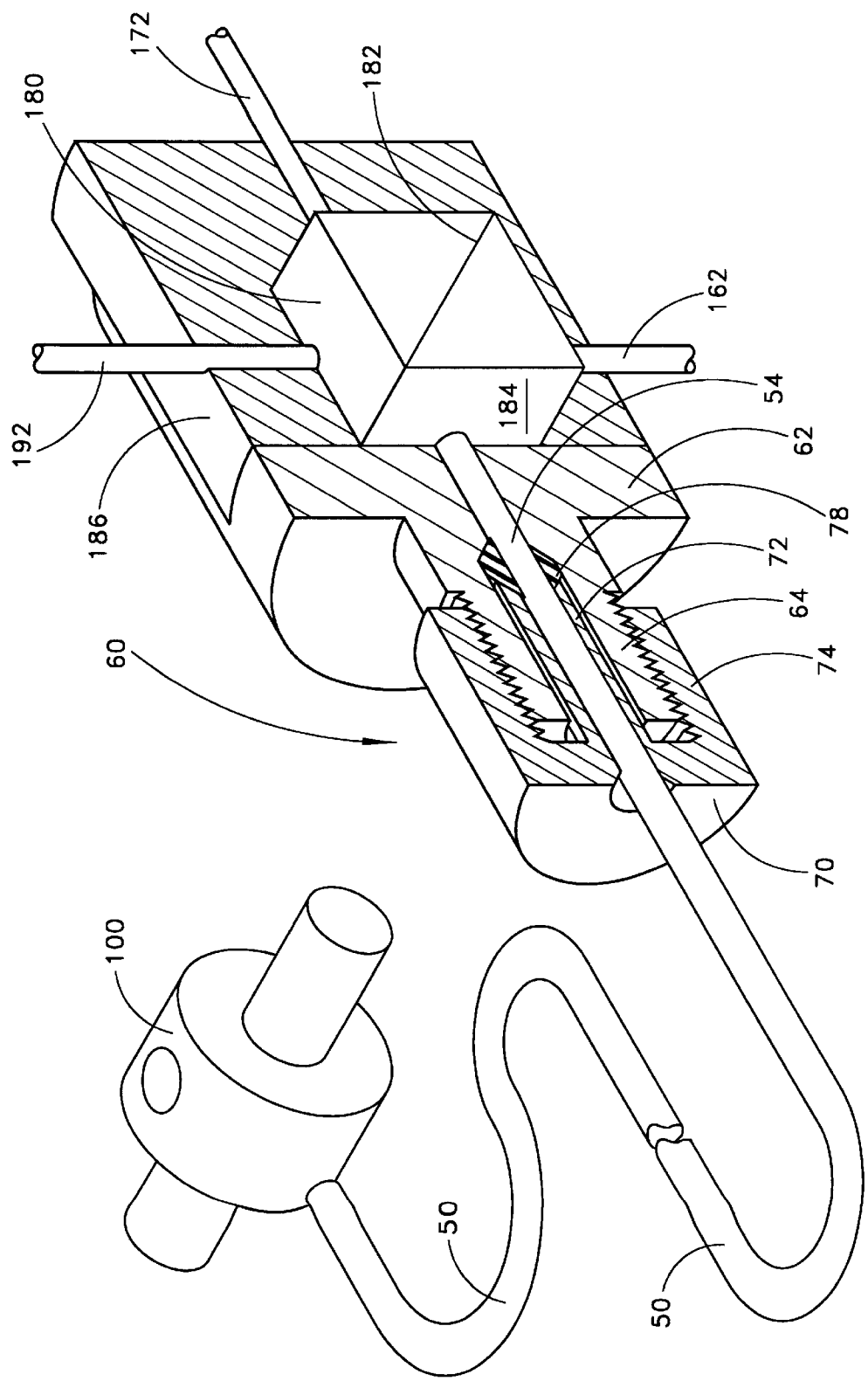
FIG. 17 is a simplified perspective view similar to FIG. 16, but showing a monofilament optical fiber optically coupled to the beam splitter.

FIGS. 16 and 17 show the fiber optic connector 60 of FIGS. 14 and 15 in more detail. FIG. 16 shows the connector 60 prior to insertion of the distal end portion 54 of the optical fiber 50. FIG. 17 shows the connector 60 with the distal end portion 54 of the optical fiber 50 inserted into the connector 60 and releasably optically coupled to the beam splitter 180.

This fiber optic connector 60 includes a base 62, which can be mounted on the front panel 152, as shown in FIGS. 14 and 15. The mounting block 186 can be secured to the base 62 to hold the front face 184 of the beam splitter 180 against the base 62. The base 62 includes an externally threaded stem 64 which extends forwardly of the base 62. An elongate channel 66 extends through the stem 64 and the front portion of the base 62, terminating at the front face 184 of the beam splitter 180. The inner diameter of this channel 66 is greater throughout most of the length of the stem 64 than it is in the base so it may accommodate a tubular projection 72 of the cap 70 (discussed immediately below) within the stem, yet closely receive a length of the optical fiber 50 in the front portion of the base 62.

A locking cap 70 is adapted to releasably retain the distal end portion 54 of the optical fiber 50 within the channel 66 of the base 62. The cap 70 has an internally threaded annular flange 74 which is designed to mate with the externally threaded stem 64. As mentioned above, the cap also has an elongate tubular projection 72 extending rearwardly within the annular flange 74. The space between the annular flange 74 and the projection 72 of the cap should be sufficient to accommodate the stem 64 of the base 60 therebetween. The projection 72 has a channel 76 extending along its length, with the channel being sized to fairly closely receive the distal end portion 54 of the optical fiber 50 therein.

The fiber optic connector 60 also has a locking collar 78 formed of a resiliently compressible material. The locking collar 78 is disposed within the channel 66 of the stem 64 just in front of the smaller diameter portion of the channel 66. The locking collar 78 is longitudinally compressible between the tubular projection 72 of the cap 70 and the base 62. In its relaxed state (shown in FIG. 16), the locking collar 78 has an inner diameter slightly greater than the outer diameter of the optical fiber 50. This permits the distal end portion 54 of the optical fiber to slide within the channel 76 in the cap and the channel 66 in the base when the optical fiber 50 is inserted into or pulled out of the fiber optic connector 60.

When using the fiber optic connector 60 to optically couple the optical fiber 50 to the beam splitter 180, the distal end portion 54 of the optical fiber 50 is first inserted into the opening in the face of the cap 70. Then, the optical fiber 50 is pushed distally along the aligned channels 76 and 66 until the distal end of the optical fiber 50 abuts the front face 184 of the beam splitter 180. In this position, the distal end portion 54 of the optical fiber will be received in the channels 76 and 66 of the fiber optic connector 60. By turning the cap 70 with respect to the base 62, the locking collar 78 can be compressed between the base 62 and the tubular projection 72 of the cap 70. When compressed, the locking collar 78 will deform. Since it is constrained against expanding outwardly, it will expand inwardly until it clamps tightly against the exterior surface of the distal end portion 54 of the optical fiber 50 to hold it in place.

To remove the optical fiber 50 from the fiber optic connector 60, the operator need only loosen the cap 70. This will permit the locking washer to resiliently return to its uncompressed state, thereby releasing the distal end portion 54 of the optical fiber 50 so it may be withdrawn from the channels 66 and 76 of the fiber optic connector 60.

Figure 18:
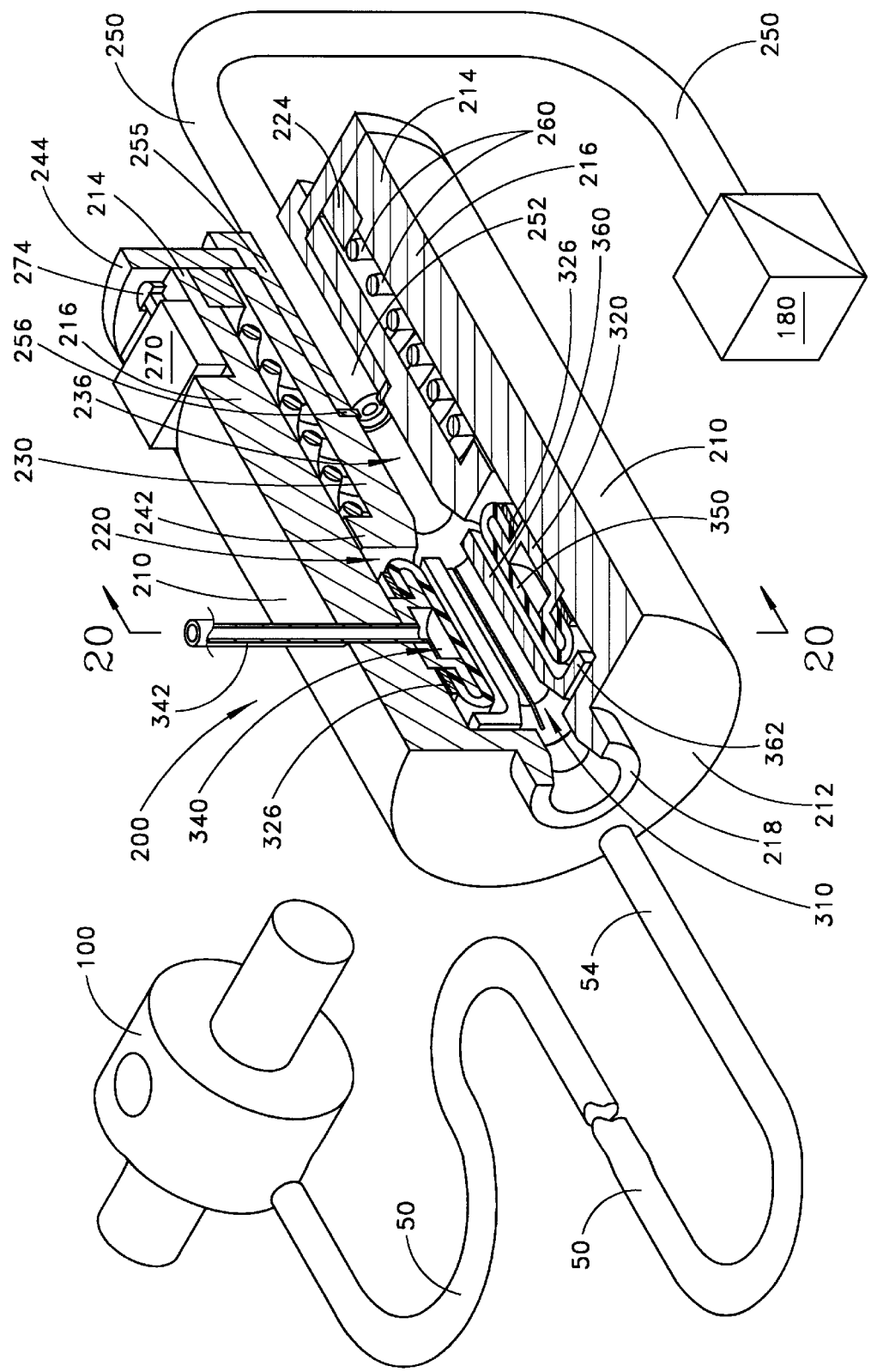
FIG. 18 is a simplified perspective, cross sectional view of an alternative fiber optic connector of the invention.
Figure 19:
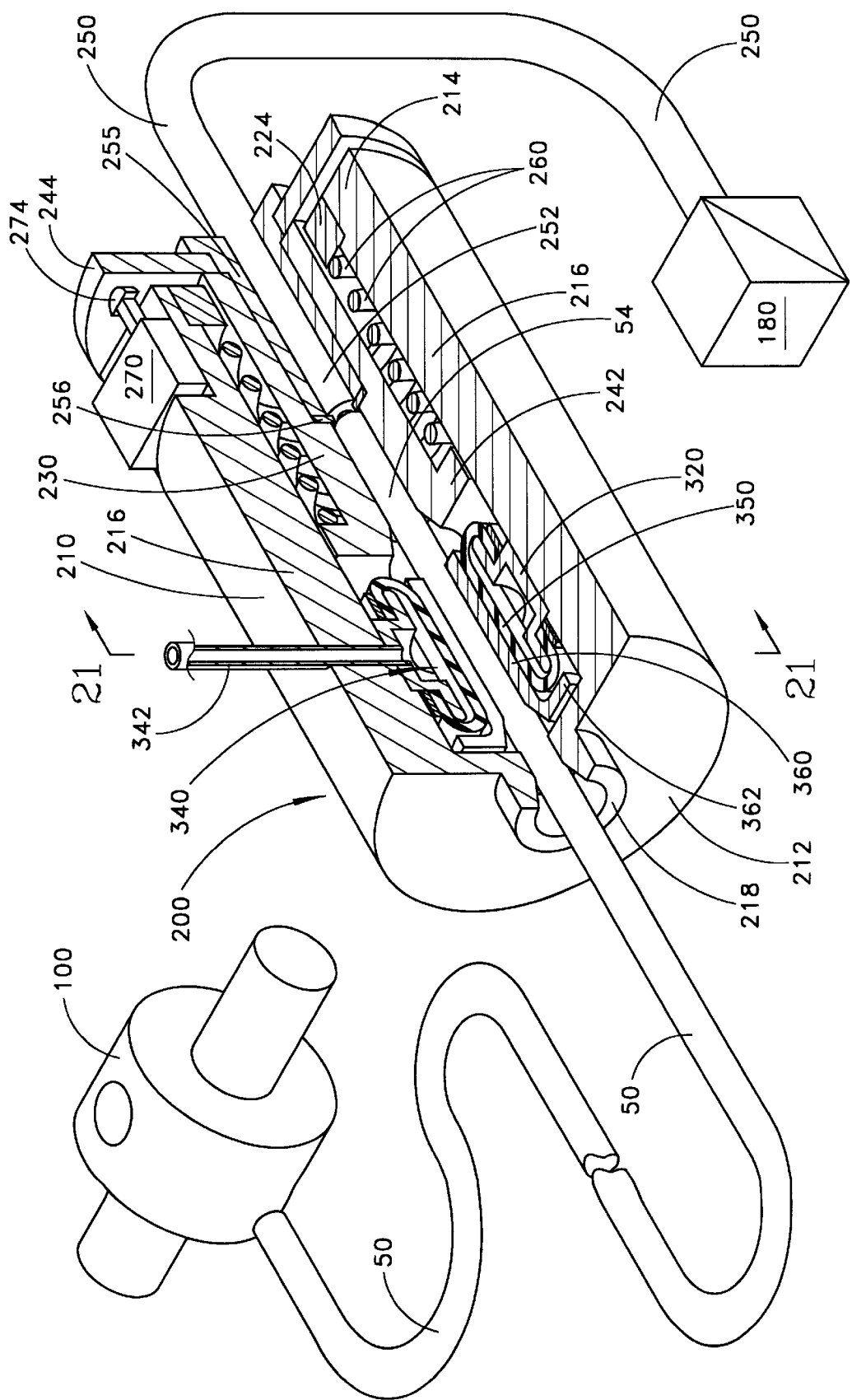
FIG. 19 is a simplified perspective view similar to FIG. 18, but showing the optical fiber optically coupled to the flexible light guide.

FIGS. 18 and 19 schematically illustrate a particularly preferred fiber optic connector 200 of the invention. In FIG. 18, the distal end portion 54 of the optical fiber 50 is spaced from the fiber optic connector 200. FIG. 19 illustrates the distal end portion 54 of the optical fiber 50 releasably retained in the fiber optic connector 200. This fiber optic connector 200 is particularly useful to releasably optically couple the optical fiber 50 of the disposable device shown in FIG. 11 to a non-disposable control module. Therefore, FIGS. 18 and 19 schematically illustrate both the optical reflector 100 and beam splitter 180 discussed above. However, it is to be understood that the fiber optic connector 200 can be used in any situation where it is necessary to releasably optically couple an optical fiber to another optical component.

The fiber optic connector 200 includes a housing 210 which has a proximal end 212 and a distal end 214. The housing 210 is desirably generally cylindrical in shape with its tubular wall 216 defining an elongated internal chamber 220 extending along most of the length of the housing. In the illustrated embodiment, the housing 210 also includes an internally tapered inlet 218 to facilitate insertion of the optical fiber 50 into the fiber optic connector 200. Adjacent its distal end 214, the housing may be provided with an annular ring 224 that extends radially inwardly of the tubular wall 216. This annular ring 224 defines a distal surface that abuts the distal end of a coil spring 260.

A light guide carriage 230 is slidably received within the internal chamber 220 of the housing 210. This light guide carriage 230 has an elongated bore 236 which extends longitudinally between proximal and distal ends of the light guide carriage. In the illustrated embodiment, the body of the light guide carriage 230 has the same cross-sectional shape as the internal chamber 220 of the housing 210. Optimally, both the elongated internal chamber 220 and the light guide carriage 230 are generally cylindrical in shape.

The body of the light guide carriage 230 has an external diameter substantially smaller than the diameter of the internal chamber 220 of the housing 210. As a result, the tubular wall 216 of the housing and the body of the light guide carriage 230 define an elongated annular space within which a resilient element (e.g., the coil spring 260) may be retained to bias the light guide carriage 230 proximally with respect to the housing 210. Although in the illustrated embodiment the biasing resilient element comprises a coil spring 260, the resilient element may be comprised of any structure which is able to bias the light guide carriage 230 proximally with respect to the housing 210. A flange 242 may extend radially outwardly from the proximal end of the light guide carriage 230, defining a proximal surface which abuts the proximal end of the coil spring 260. The coil spring 260 is thus disposed between the annular ring 224 of the housing and the flange 238 of the light guide carriage. The coil spring 260 serves to urge the annular ring 224 of the housing 210 and the flange 238 of the light guide carriage 230 away from one another, thereby biasing the light guide carriage 230 proximally with respect to the housing 210.

As discussed more fully below, to releasably retain the optical fiber 50 in the fiber optic connector 200, an operator will urge the distal end portion 54 of the optical fiber distally within the connector until the distal end of the optical fiber 50 pushes the light guide carriage 230 distally a predetermined distance. A position detector 270 can be used to monitor the position of the light guide carriage 230 with respect to the housing 210 and generate a clamp actuating signal upon detecting a predetermined change in the relative positions of the light guide carriage 230 and the housing 210. A wide variety of mechanisms can be used to detect the change in position of the light guide carriage 230 with respect to the housing 210 and generate a clamp actuating signal. For example, electromechanical or photoelectric position detectors can be used. Photoelectric sensors which can be used as position detectors are widely commercially available, such as from Banner Engineering Corporation, Minneapolis, Minn., USA.

In the embodiment of FIGS. 18 and 19, the position detector 270 comprises an electromechanical position detector 270 mounted on the exterior of the housing 210. The illustrated electromechanical position detector 270 has a distally biased actuator 274. In FIG. 18, the actuator is biased distally into engagement with a control surface of the light guide carriage 230. In the embodiment of FIGS. 18 and 19, the control surface of the light guide carriage 230 comprises a proximal face of an annular plate 244 extending radially outwardly at the distal end of the light guide carriage. As the light guide carriage 230 is urged distally with respect to the housing, the annular plate 244 moves farther away from the position detector 270, thereby permitting the actuator 274 to move distally. When the actuator 274 moves a predetermined distance, the position detector 270 generates an electrical clamp actuating signal which causes the clamp to close on the optical fiber and hold it in place.

The electromechanical position detector 270 shown in FIGS. 18 and 19 is physically attached to the housing 210. However, the position detector can be associated with either the housing 210 or the light guide carriage 230. For example, the electromechanical position detector 270 of FIGS. 18 and 19 could be attached to the light guide carriage 230 instead of the housing 210 and have an actuator which extends proximally into engagement with the housing.

Preferably, the position detector 270 is physically attached directly to either the housing or the light guide carriage. Such a direct physical attachment is not necessary, though. As noted above in connection with FIGS. 14 and 15, the fiber optic connector 60 of that embodiment can be mounted on the front panel 152 of an enclosure for a control module 150. If the present fiber optic connector 200 were used instead, the housing 210 could be mounted on the front panel 152 of the control module enclosure and the position detector 270 could be secured to the enclosure at a location close to the distal end of the light guide carriage 230. Such an indirect physical association between the position detector 270 and one of the housing 210 and the light guide carriage 230 will suffice so long as it permits the position detector to detect the predetermined change in the relative positions of the light guide carriage 230 and housing 210.

The fiber optic connector 200 includes a flexible light guide 250. This flexible light guide 250 has a proximal end portion 252 which is permanently secured within a distal end portion of the light guide carriage 230 and extends distally from the light guide carriage. The proximal end portion 252 of the light guide 250 can be secured within the elongated bore 236 of the light guide carriage 230 in any suitable fashion, e.g., by gluing it in place. In the embodiment of FIGS. 18 and 19, the proximal end portion 252 of the flexible light guide 250 is provided with an additional fitting 255 that helps secure the light guide in the distal portion of the light guide carriage 230. This same fitting 255 can also hold the annular plate 244 on the light guide carriage 230.

FIGS. 18 and 19 show a spacer ring 256 positioned between the proximal end of the fitting 255 and the body of the light guide carriage 230. This spacer ring extends radially inwardly into the elongated bore 236 at the proximal end of the light guide 250 far enough to contact the distal end of the optical fiber 50 when the optical fiber 50 is inserted in the fiber optic connector 200. This will prevent the polished ends of the light guide 250 and the optical fiber 50 from contacting one another. The spacer ring 256 should be relatively thin, though, to ensure that the light guide 250 and the optical fiber 50 are optically coupled when the distal end of the optical fiber 50 abuts the spacer ring 256.

The distal end of the flexible light guide 250 can be attached to an optical element, such as the beam splitter 180 shown schematically in FIGS. 18 and 19. The beam splitter 180 can be held in a fixed position with respect to the housing 210 of the fiber optic connector 200 by separately mounting both the housing 210 and the beam splitter 180 on a wall of a control module 150. The flexible light guide 250, however, should be free to flex along its length to accommodate movement of the light guide carriage 230 with respect to the beam splitter 180. This flexible light guide 250 may comprise a single, monofilament optical fiber or a cable comprising a bundle of individual optical fibers, as is known in the art.

Figure 20:
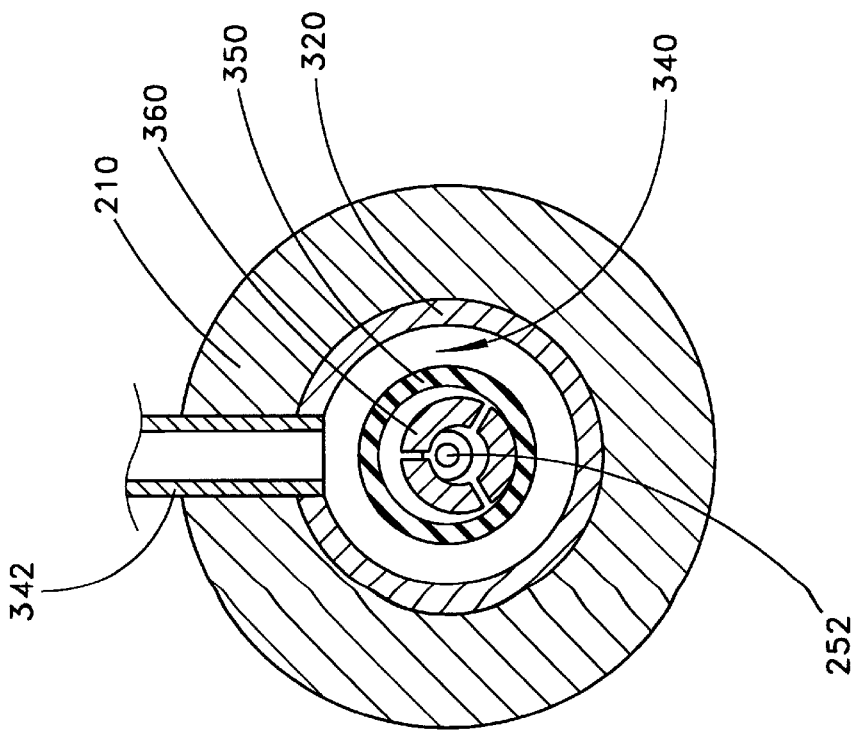
FIG. 20 is a transverse cross sectional view of the fiber optic connector taken along line 20—20 in FIG. 18 and showing the pneumatic clamp in its open position.

The present embodiment of the fiber optic connector 200 also includes a clamp carried by the housing proximally of the light guide carriage 230. This clamp defines a channel 310 through which the distal end portion 54 of the optical fiber 50 may be advanced. The clamp has an open position (shown in FIGS. 18 and 20) wherein the distal end portion 54 of the fiber may be moved freely along the channel 310 and a closed position (shown in FIGS. 19 and 21) wherein the clamp prevents free movement of the optical fiber.

Any suitable clamp can be employed. It need only be able to move from the open position to the closed position in response to the clamp actuating signal generated by the position detector. For example, an electromechanical clamp can be utilized.

FIGS. 18–21 illustrate one particularly preferred embodiment of a clamp which employs a pneumatic chamber to selectively hold the distal end portion 54 of the optical fiber within the fiber optic connector 200. This pneumatic chamber is generally toroidal in shape and is defined by a rigid tubular housing 320 and a resilient, distendable inner wall 350. A toroidal pneumatic cavity 340 is defined between the tubular housing 320 and the tubular inner wall 350. A gas conduit 342 is adapted to deliver compressed gas to the pneumatic cavity 340 from a compressed gas source, as detailed below.

The inner wall 350 can be attached to the rigid tubular housing in any desired fashion. In the embodiment illustrated in FIGS. 18–21, the inner wall 350 can be made from an elastic tube. This elastic tube is positioned within the tubular housing 320 and each end of the tube is folded over a corresponding end of the tubular housing 320. Each end of the elastic tube is clamped in place about the exterior surface of the tubular housing 320 by an annular compression ring 326. The elastic tube used to form the inner wall 350 can be formed of rubber, e.g., silicone rubber.

Compressed gas is delivered to the toroidal cavity 340 through the gas conduit 342. As the pneumatic chamber is pressurized, the inner wall 350 will extend radially inwardly, as shown schematically in FIGS. 19 and 21. In the embodiment of FIGS. 18–21, the clamp also includes a plurality of clamping pads 360 disposed radially inwardly of the inner wall 350 of the toroidal pneumatic chamber. Since they are disposed inwardly of the inner wall, the clamping pads 360 actually define the channel 310 of the clamp in this embodiment. When the clamp is in its open position (FIGS. 18 and 20), the clamping pads 360 are spaced apart sufficiently to permit the distal end portion 54 of the optical fiber to be easily advanced into the channel 310. When the pneumatic chamber is pressurized to move the clamp into its closed position (FIGS. 19 and 21), the inner wall 350 distends radially inwardly and urges the clamping pads against the exterior surface of the distal end portion 54 of the optical fiber 50.

The clamping pads 360 are provided with tabs 362 extending radially outwardly from their proximal ends. The tabs 362 of the clamping pads 360 can be attached to one another, thereby interconnecting the proximal ends of the pads. As best seen in FIG. 18, this presents a single collet-type structure with an inner diameter which is slightly larger than the outer diameter of the distal end portion 54 of the optical fiber. When the cavity 340 is pressurized, the inner wall 350 will urge the clamping pads 360 radially inwardly against the exterior surface of the distal end portion 54 of the optical fiber, as shown in FIGS. 19 and 21.

Figure 21:
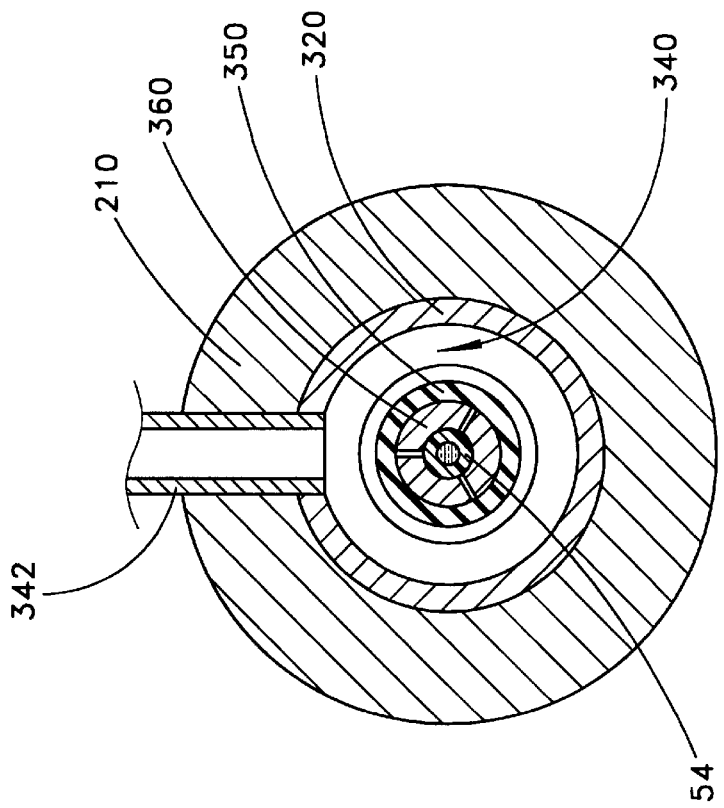
FIG. 21 is a transverse cross sectional view of the fiber optic connector taken along line 21—21 in FIG. 19 and showing the pneumatic clamp in its closed position.

While the number of clamping pads 360 can be varied as desired, the embodiment of FIGS. 18–21 employs three such pads. The clamping pads 360 may be arcuate in cross section to permit just three pads to substantially completely surround the exterior of the distal end portion 54 of the optical fiber when the clamp is in its closed position, as best seen in FIG. 21.

If so desired, however, the clamping pads 360 can be omitted. In such a clamp, the tubular inner wall 350 may directly contact the exterior of the distal end portion 54 of the optical fiber to hold it in place within the fiber optic connector 200.

Figure 22:
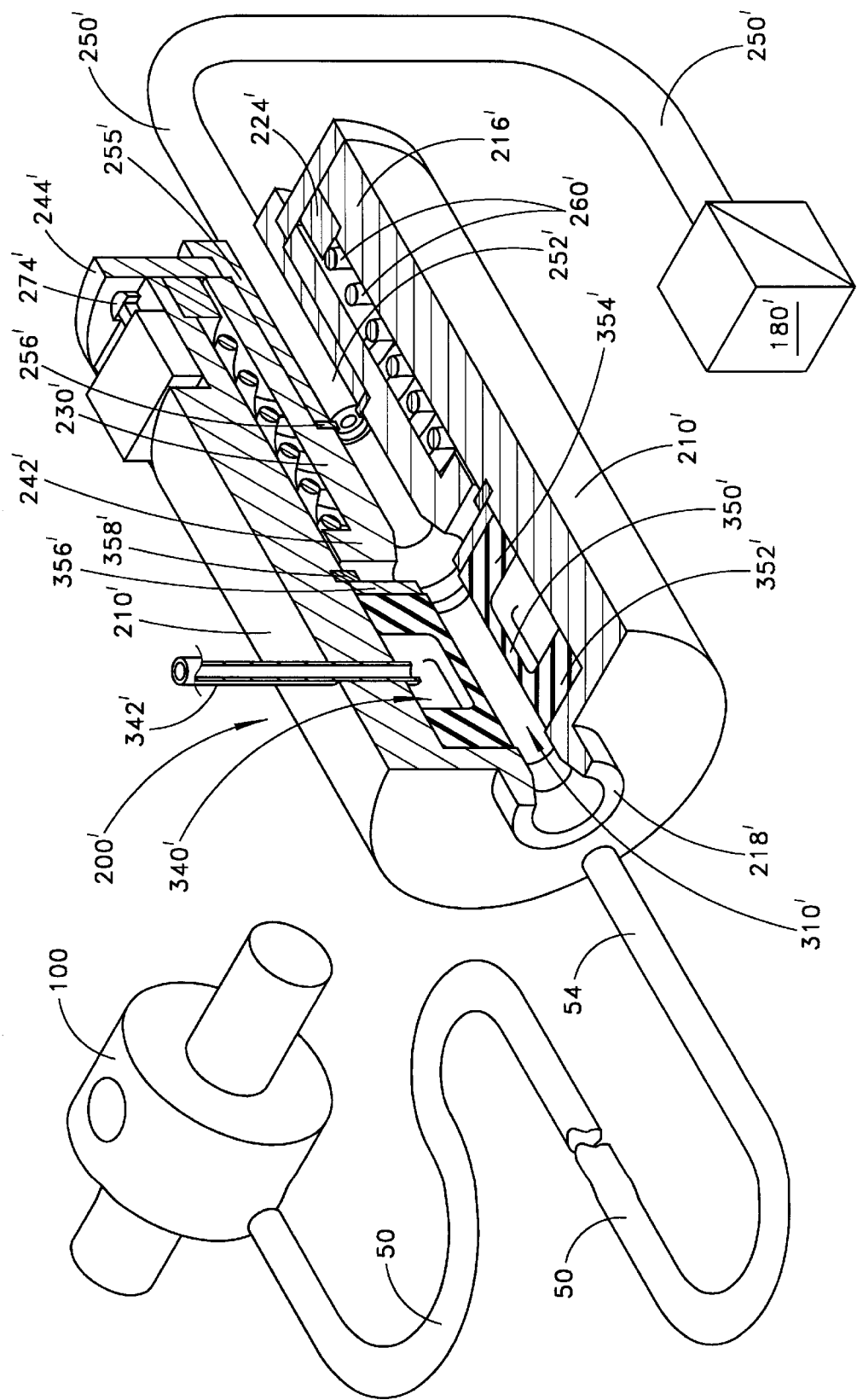
FIG. 22 is a simplified perspective, cross sectional view, similar to FIG. 18, of a fiber optic connector employing an alternative pneumatic chamber.
Figure 23:
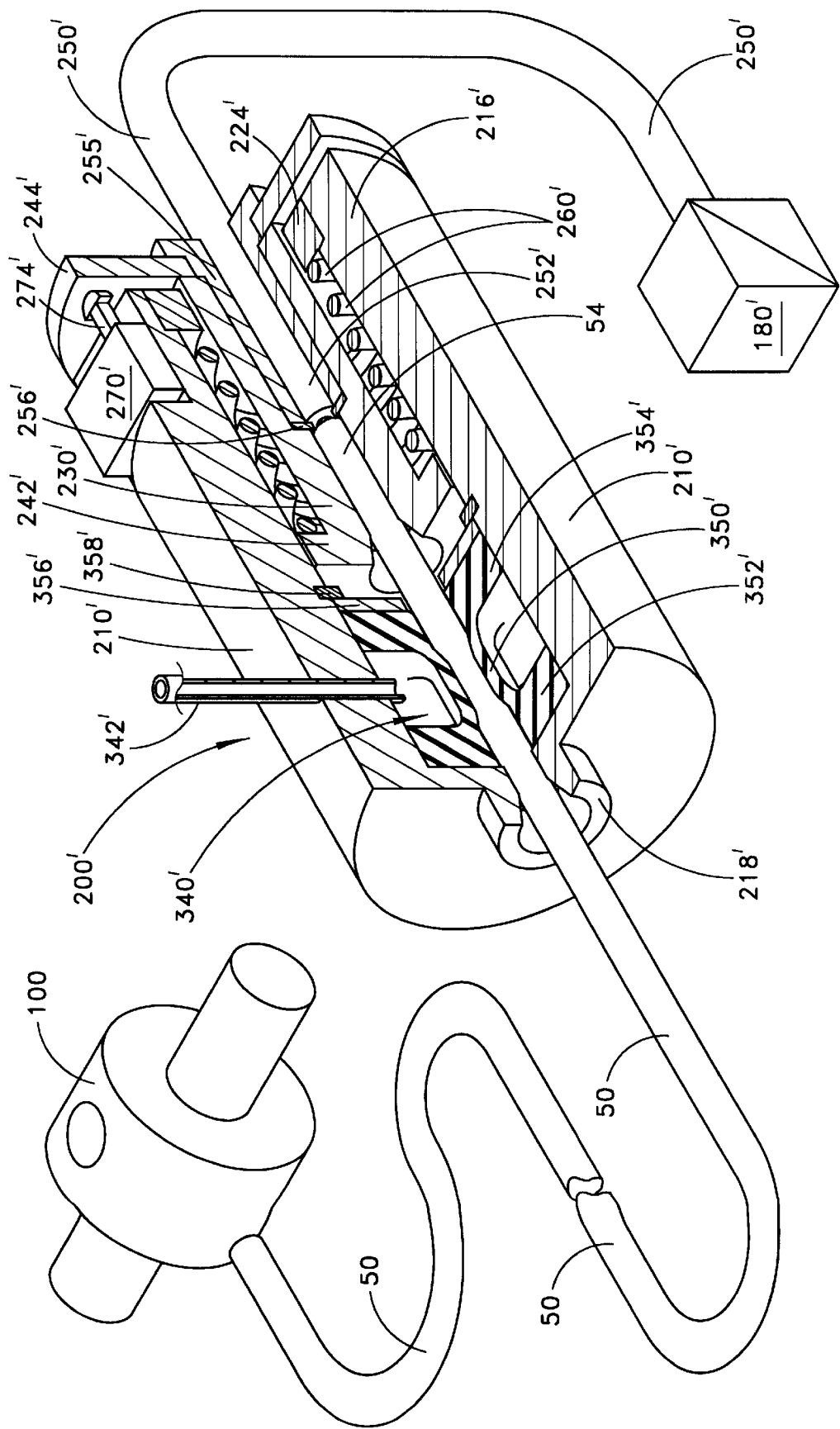
FIG. 23 is a simplified perspective view similar to FIG. 22, but showing the optical fiber optically coupled to the flexible light guide.

FIGS. 22 and 23 illustrate an alternative fiber optic connector 200' which includes a clamp having a different pneumatic chamber. In this embodiment, the thin, elastic inner wall 350' and thick proximal 352' and distal 354' walls are integrally formed from, e.g., silicon rubber. The proximal 352' and distal 354' walls extend radially outwardly at the proximal and distal ends, respectively, of the inner wall 350'. The proximal wall 352', inner wall 350' and distal wall 354' form a unitary insert which may be secured in place by an annular gasket 356' and a retaining ring 358'. A toroidal pneumatic cavity 340' is defined between this unitary insert and the wall of the housing 210'. When the pneumatic cavity 340' is pressurized, the inner wall 350' will move radially inwardly, clamping on the optical fiber 50. At the same time, the thick proximal 352' and distal 354' walls will be pressed against the front wall of the housing 210' and the annular gasket 356', respectively. The walls 352' and 354' will be compressed longitudinally, causing them to expand radially, thereby improving the seal between the unitary insert and the housing 210'. If so desired, an appropriate sealant or glue can be used to further improve the seal between the unitary insert and the housing 210'.

FIGS. 22 and 23 also illustrate how one can eliminate the clamping pads (360 in FIGS. 18–21). As shown in FIG. 23, the inner wall 350' of the pneumatic chamber is in direct contact with the distal end portion 54 of the optical fiber 50 when the clamp is in its closed position.

Regardless of what specific clamp design is used in the fiber optic connector 200 (or 200') of the invention, the clamp should move between its open and closed positions in response to a clamp actuating signal generated by the position detector 270. In operation, the user will insert the distal end of an optical fiber 50 into the internally tapered inlet 218 of the housing 210. The distal end portion 54 of the optical fiber can then be advanced through the channel 310 in the clamp and into the proximal end portion of the elongated bore 236 of the light guide carriage 230. Once the distal end of the optical fiber 50 abuts the spacer ring 256 of the light guide carriage 230, further urging of the optical fiber 50 distally will cause the light guide carriage 230 to move distally, as well.

The position sensor 270 will detect movement of the light guide carriage 230 with respect to the housing 210. Once the user urges the light guide carriage 230 proximally a predetermined distance, the position sensor 270 will generate a clamp actuating signal, as noted above. In response, the clamp will automatically move into its closed position, wherein the distal end portion 54 of the optical fiber is constrained against further movement. As a result, the optical fiber 50 and the flexible light guide 250 are optically coupled to one another simply by advancing the optical fiber 50 for a predetermined distance into the fiber optic connector 200.

One advantage of this design is that it permits a user to readily optically couple an optical fiber 50 to a light guide 250 without having to provide the optical fiber 50 with a separate fitting at its distal end. In the Rotablator® device and the Rotablator® RotaLink™ System, the distal ends of the fiber optic cables are provided with standard Hewlett-Packard type click-fit plugs which snap-fit into the housings of the light emitting diode or the light detector. A fiber optic connector 200 of the invention, however, allows one to use a basic optical fiber 50 which merely has a polished distal end. This is particularly cost effective when one intends the optical fiber 50 to be disposable after being used on just one patient.

A fiber optic connector (200 or 200') having a pneumatic chamber in accordance with the invention has utility in a wide variety of applications. However, such a fiber optic connector is particularly well suited for use in connection with a rotational atherectomy device having a gas-driven prime mover. For example, the fiber optic connector 200 of FIGS. 18–21 can be used to releasably optically couple the optical fiber 50 of the disposable device shown in FIG. 11 to a non-disposable control module. The advantage of such an arrangement is that the same source of compressed gas used to supply compressed gas to the prime mover can deliver compressed gas to the pneumatic clamp of the fiber optic connector.

Figure 24:
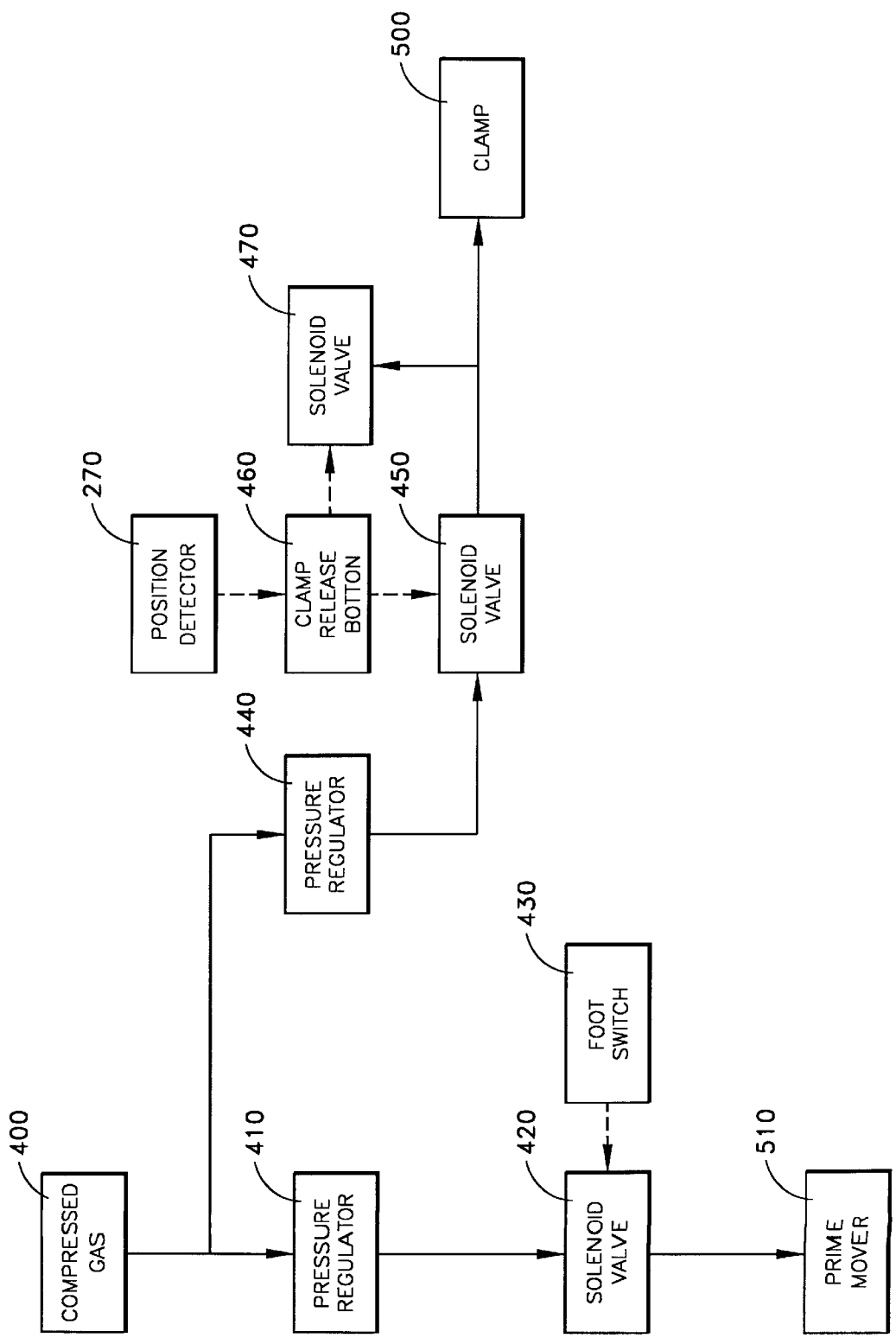
FIG. 24 is a block diagram illustrating a rotational atherectomy device of the invention which utilizes a single source of compressed gas to drive a prime mover and to actuate a pneumatic clamp.

FIG. 24 schematically illustrates how the pneumatic clamp of a fiber optic connector 200 and the prime mover of the device shown in FIGS. 7–13 may be operatively connected to the same source of compressed gas. In FIG. 24, solid lines are intended to designate pneumatic connections between components while dashed lines are intended to designate electrical connections between components.

In FIG. 24, the source of compressed gas 400 is connected to a pair of pressure regulators 410 and 440. Typically, the source of compressed gas will be a cylinder of compressed gas, e.g., a tank of compressed nitrogen or air. The pressure regulator 410 controls the pressure of the compressed gas delivered to the prime mover 510 to adjust the rotational speed of the prime mover 510. The compressed gas from the pressure regulator 410 is delivered to a solenoid valve 420. (While solenoid valves are believed suitable for this purpose, it should be understood that any valve which can selectively control the delivery of compressed gas could be used instead.) The solenoid valve 420 controls delivery of compressed gas to the prime mover 510. Typically, the normally closed solenoid valve 420 will be operatively connected to a foot pedal 430 or other control manipulated by the operator to selectively open the valve 420 to supply gas to the prime mover 510 of the rotational atherectomy device.

The other pressure regulator 440 maintains the pressure of the compressed gas delivered to a solenoid valve 450 which controls delivery of compressed gas to the pneumatic clamp 500 of the fiber optic connector 200. As explained above, the position detector 270 monitors the relative positions of the housing 210 and the light guide carriage 230 of the fiber optic connector 200. The position detector 270 will deliver a clamp actuating signal when the light guide carriage 230 moves a sufficient distance with respect to the housing 210 to indicate that the distal end portion 54 of the optical fiber 50 has been properly seated in the fiber optic connector 200. This clamp actuating signal causes the normally closed solenoid valve 450 to open and deliver compressed gas to the pneumatic chamber of the clamp 500, moving the clamp to its closed position to retain the distal end portion 54 of the optical fiber 50 in the fiber optic connector 200.

To release the distal end portion 54 of the optical fiber 50 from the fiber optic connector 200, the pneumatic clamp 500 will have to be released. A separate clamp release button 460 and a normally closed solenoid valve 470 may be used to release the pneumatic clamp 500. Desirably, the clamp release button includes two electrical switches—a normally closed switch which electrically connects the position detector 270 to the solenoid valve 450 and a normally open switch which, when closed, opens the solenoid valve 470. When the clamp release button 460 is actuated, the solenoid valve 450 will close and the solenoid valve 470 will open, thereby venting compressed gas from the pneumatic clamp 450 to the ambient atmosphere. This will depressurize the pneumatic clamp, thereby releasing the optical fiber 50. The fiber optic connector 200 of FIGS. 18–21 includes a coiled spring 260 which biases the light guide carriage 230 proximally with respect to the housing 210. When the clamp releases the distal end portion 54 of the optical fiber 50, the light guide carriage 230 will automatically move distally, thereby opening the switch of the position detector 270. As a consequence, the clamp will remain in its open position even after the clamp release button 460 is allowed to return to its normal position, permitting the user to remove the distal end portion 54 of the optical fiber 50 from the fiber optic connector 200.

The clamp release button 460 described above can be a standard mechanical push button, but alternatives such as a photoelectric touch switch or the like would also suffice. Suitable photoelectric touch switches are commercially available from Banner Engineering Corporation, Minneapolis, Minn., USA.

While a preferred embodiment of the present invention has been described, it should be understood that various changes, adaptations and modifications may be made therein without departing from the spirit of the invention and the scope of the appended claims.

What is claimed is:

1. A rotational atherectomy device, comprising:
    a) a prime mover having a prime mover shaft;
    b) a flexible drive shaft rotatable together with the prime mover;
    c) a handle having a prime mover carriage which carries the prime mover; and
    d) a generally cylindrical optical reflector mounted on the prime mover shaft, the reflector having a light-reflective outer surface, a longitudinal bore through which the prime mover shaft extends and a transverse bore extending through the reflector along an axis which is generally perpendicular to the prime mover shaft so that the prime mover shaft obstructs passage of light along the axis of the transverse bore.

2. A rotational atherectomy device, comprising:
    a) a prime mover having a prime mover shaft;
    b) a flexible drive shaft rotatable together with the prime mover;
    c) a handle having a prime mover carriage which carries the prime mover;
    d) a generally cylindrical optical reflector mounted on the prime mover shaft, the reflector having a light-reflective outer surface, a longitudinal bore through which the prime mover shaft extends and a transverse bore extending through the reflector along an axis which is generally perpendicular to the prime mover shaft so that the prime mover shaft obstructs passage of light along the axis of the transverse bore;
    e) a light source and a light detector positioned externally of the handle;
    f) a single, monofilament optical fiber having proximal and distal ends, the proximal end of the optical fiber being permanently secured within the prime mover carriage adjacent the cylindrical reflector such that an axis of a proximal end portion of the optical fiber intermittently becomes generally aligned with the axis of the transverse bore as the cylindrical reflector is rotated together with the prime mover, and the distal end of the optical fiber being adapted to be releasably optically coupled to both the light source and the light detector such that the single, monofilament optical fiber both receives light emitted by the light source and returns to the light detector light reflected from the cylindrical reflector.

3. The rotational atherectomy device of claim 2 wherein the optical fiber is optically coupled to the light source and the light detector via a beam splitter positioned externally of the handle, the beam splitter directing into the optical fiber a predetermined percentage of the light emitted by the light source and delivering to the light detector a predetermined percentage of the light reflected from the cylindrical reflector back into the optical fiber.

4. A rotational atherectomy device, comprising:
    a) a prime mover having a prime mover shaft;
    b) a flexible drive shaft rotatable together with the prime mover;
    c) a handle having a prime mover carriage which carries the prime mover;
    d) a generally cylindrical optical reflector mounted on the prime mover shaft, the reflector having a light-reflective outer surface, a longitudinal bore through which the prime mover shaft extends and a transverse bore extending through the reflector along an axis which is generally perpendicular to the prime mover shaft so that the prime mover shaft obstructs passage of light along the axis of the transverse bore, e) a light source and a light detector positioned externally of the handle;

f) a single, monofilament optical fiber having proximal and distal ends, the proximal end of the optical fiber being permanently secured within the prime mover carriage adjacent the cylindrical reflector such that an axis of a proximal end portion of the optical fiber intermittently becomes generally aligned with the axis of the transverse bore as the cylindrical reflector is rotated together with the prime mover, and the distal end of the optical fiber being adapted to be releasably receivable within a non-disposable fiber optic connector for releasable optical coupling to a proximal end of a flexible light guide, the flexible light guide having a distal end which is permanently optically coupled to both the light source and the light detector.

5. The rotational atherectomy device of claim 4 wherein the flexible light guide is optically coupled to both the light source and the light detector via a fiber optic coupler positioned externally of the handle.

6. The rotational atherectomy device of claim 4 wherein the flexible light guide is optically coupled to the light source and the light detector via a beam splitter positioned externally of the handle, the beam splitter directing into the flexible light guide a predetermined percentage of the light emitted by the light source and delivering to the light detector a predetermined percentage of the light reflected from the cylindrical reflector back into the optical fiber.

7. The rotational atherectomy device of claim 6 wherein the beam splitter comprises a glass beam splitting cube.

8. A fiber optic connector comprising:

a) a housing having proximal and distal ends and defining an elongate internal chamber;

b) a light guide carriage having proximal and distal ends and slidably received within the chamber of the housing, the light guide carriage defining an elongated bore extending between the ends of the carriage;

c) a resilient element biasing the carriage proximally with respect to the housing;

d) a flexible light guide having a proximal end portion permanently secured within a distal end portion of the elongated bore of the carriage;

e) at least one optical fiber which may be releasably optically coupled to the flexible light guide;

f) a clamp carried by the housing proximally of the light guide carriage, the clamp defining a channel through which a distal end portion of the optical fiber may be advanced into a proximal end portion of the elongated bore of the carriage such that the optical fiber is optically coupled to the flexible light guide, the clamp being selectively moveable between an open position wherein the optical fiber may be moved freely along the channel of the clamp and a closed position wherein the clamp prevents free movement of the optical fiber, the clamp moving from its open position to its closed position in response to a clamp actuating signal; and g) a position detector associated with one of the housing and the carriage and adapted to generate the clamp actuating signal upon detecting a predetermined change in position of the carriage with respect to the housing.

9. The connector of claim 8 wherein the resilient element comprises a coil spring disposed about the carriage.

10. The connector of claim 9 wherein the carriage and the housing include opposing spring abutting surfaces, the coil spring being disposed between these opposing spring abutting surfaces.

11. The connector of claim 8 wherein the clamp comprises a pneumatic chamber.

12. The connector of claim 11 wherein the pneumatic chamber is toroidal in shape, the toroidal pneumatic chamber having an inner wall which is adapted to move radially inwardly as the chamber is pressurized.

13. The connector of claim 12 wherein the clamp assumes its closed position when the pneumatic chamber is pressurized.

14. The connector of claim 13 wherein the clamp further comprises a plurality of clamping pads disposed radially inwardly of the inner wall of the toroidal pneumatic chamber, the clamping pads together both defining the channel of the clamp and clamping the optical fiber when the pneumatic chamber is pressurized.

15. The connector of claim 8 wherein the position detector comprises an electromechanical switch.

16. The connector of claim 8 wherein the position detector comprises a photoelectric sensor.

17. An optical tachometer for an atherectomy device, comprising:

a) at least one optical reflector rotatable together with a shaft of a prime mover;

b) at least one optical fiber having a proximal end which is permanently secured within a prime mover carriage adjacent to the optical reflector; and c) a fiber optic connector comprising
   i) a housing having proximal and distal ends and defining an elongate internal chamber;
   ii) a light guide carriage having proximal and distal ends and slidably received within the chamber of the housing, the light guide carriage defining an elongated bore extending between the ends of the carriage, a length of a flexible light guide being permanently received within a distal end portion of the bore;
   iii) a clamp carried by the housing proximally of the light guide carriage, the clamp defining a channel through which a distal end portion of the optical fiber may be advanced into a proximal end portion of the elongated bore of the carriage such that the optical fiber is optically coupled to the flexible light guide, the clamp being selectively moveable between an open position wherein the optical fiber may be moved freely along the channel of the clamp and a closed position wherein the clamp prevents free movement of the optical fiber, the clamp moving from its open position to its closed position in response to a clamp actuating signal; and
   iv) a position detector carried by one of the housing and the carriage and adapted to generate the clamp actuating signal upon detecting a predetermined change in position of the carriage with respect to the housing.

18. A rotational atherectomy device comprising:

a) a source of compressed gas;

b) a gas driven prime mover operatively connected to the source of compressed gas;

c) a handle having a prime mover carriage which carries the prime mover;

d) a flexible drive shaft rotatable together with the prime mover;

e) at least one optical reflector rotatable together with the prime mover;

f) a pneumatic clamp which is operatively connected to the same source of compressed gas which is driving the prime mover;

g) an optical fiber having a proximal end which is secured within the prime mover carriage adjacent the optical reflector and a distal end portion which is adapted to be releasably retained by the pneumatic clamp;

h) a light source and a light detector positioned externally of the handle and adapted to be optically coupled to the optical fiber when the optical fiber is retained by the pneumatic clamp.

* * * * *